United States Patent
Akeson et al.

(10) Patent No.: US 6,936,433 B2
(45) Date of Patent: Aug. 30, 2005

(54) METHODS AND DEVICES FOR CHARACTERIZING DUPLEX NUCLEIC ACID MOLECULES

(75) Inventors: Mark Akeson, Santa Cruz, CA (US); Wenonah Vercoutere, Santa Cruz, CA (US); David Haussler, Santa Cruz, CA (US); Stephen Winters-Hilt, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 263 days.

(21) Appl. No.: 09/990,102

(22) Filed: Nov. 21, 2001

(65) Prior Publication Data

US 2003/0099951 A1 May 29, 2003

Related U.S. Application Data

(60) Provisional application No. 60/253,393, filed on Nov. 27, 2000.

(51) Int. Cl.[7] ............................. C12Q 1/37; C12Q 1/00; C12Q 1/68; G01N 33/53
(52) U.S. Cl. ............................. 435/23; 435/24; 435/6; 435/4; 435/975
(58) Field of Search ............................. 435/23, 24, 6, 435/4, 975

(56) References Cited

U.S. PATENT DOCUMENTS

| | | | |
|---|---|---|---|
| 5,573,905 A | 11/1996 | Lerner et al. | |
| 5,723,598 A | 3/1998 | Lerner et al. | |
| 5,760,190 A | 6/1998 | Cigan et al. | ................. 530/370 |
| 6,015,714 A | 1/2000 | Baldarelli et al. | |

FOREIGN PATENT DOCUMENTS

| | | |
|---|---|---|
| WO | WO 96/29593 | 9/1996 |
| WO | WO 98/35012 | * 8/1998 |
| WO | WO00/28312 | 5/2000 |
| WO | WO 01/18251 | 3/2001 |
| WO | WO 01/42782 | 6/2001 |

OTHER PUBLICATIONS

Burges et al., "A Tutorial on Support Vector Machines for Pattern Recognition" Data Mining and Knowledge Discovery, Kluwer Academic Publishers, Netherlands, 2(2):121–167 (1998).

Deamer et al., "Characterization of Nucleic Acids by Nanopore Analysis" *Acc. Chem. Res.* 35:817–825 (2002).

Deamer et al., "Nanopores and nucleic acids: prospects for ultrarapid sequencing" *Trends in Biotechnology* 18:147–151 (Apr. 2000).

(Continued)

*Primary Examiner*—Louise N. Leary
(74) *Attorney, Agent, or Firm*—Bret E. Field, Bozicevic, Field & Francis LLP

(57) ABSTRACT

Methods and devices are provided for characterizing a duplex nucleic acid, e.g., a duplex DNA molecule. In the subject methods, a fluid conducting medium that includes a duplex nucleic acid molecule is contacted with a nanopore under the influence of an applied electric field and the resulting changes in current through the nanopore caused by the duplex nucleic acid molecule are monitored. The observed changes in current through the nanopore are then employed as a set of data values to characterize the duplex nucleic acid, where the set of data values may be employed in raw form or manipulated, e.g., into a current blockade profile. Also provided are nanopore devices for practicing the subject methods, where the subject nanopore devices are characterized by the presence of an algorithm which directs a processing means to employ monitored changes in current through a nanopore to characterize a duplex nucleic acid molecule responsible for the current changes. The subject methods and devices find use in a variety of applications, including, among other applications, the identification of an analyte duplex DNA molecule in a sample, the specific base sequence at a single nulceotide polymorphism (SNP), and the sequencing of duplex DNA molecules.

20 Claims, 18 Drawing Sheets

OTHER PUBLICATIONS

Vercoutere et al., "Rapid discrimination among individual DAN hairpin molecules at single–nucleotide resolution using an ion channel" *Nature Biotechnology*, 19:248–252 (Mar. 2001).

Akeson et al., Biophys.J (1999) 77:3227–3233.

Kasianowicz, et al., Proc. Natl. Acad. Sci. USA (1996) 93: 13770–13773.

Wonderlin et al., Biophys. J. (1990) 58:289–297.

* cited by examiner

Figure 6.

A) Blunt-ended DNA is attached at one end to a bead.

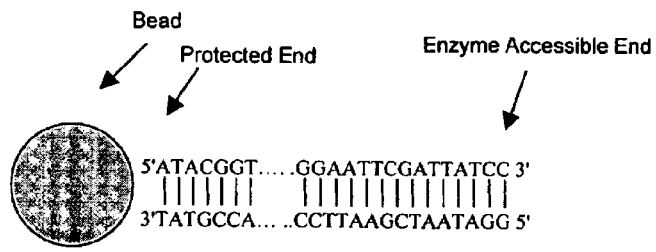

B) A single nucleotide is cut from the 3 end by a low processivity exonuclease such as exonuclease III.

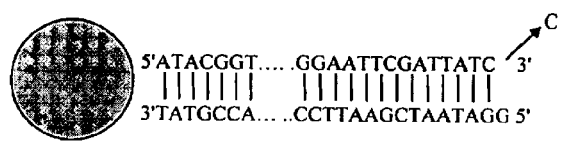

C) The single nucleotide overhang at the 5' end is read when the duplex end is captured in the nanoscale pore under an applied voltage.

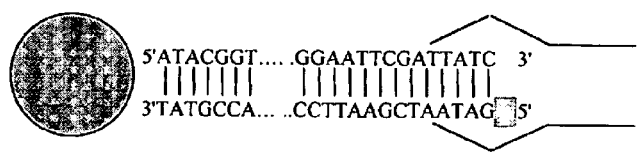

D) Once read, the DNA duplex is released from the nanopore by reversing the applied voltage.

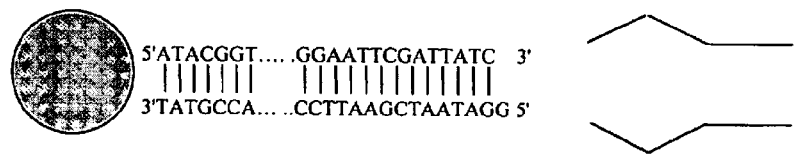

E) The single-nucleotide overhang is then cut with a nuclease (such as mung bean exonuclease), resulting in a blunt end.

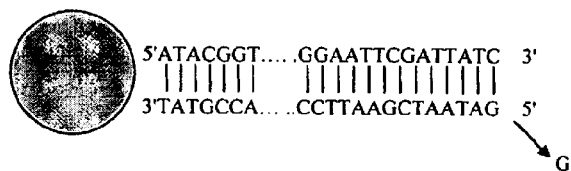

F) The blunt end is then captured and held in the nanopore by an applied voltage. The terminal base-pair is identified while the duplex is captured.

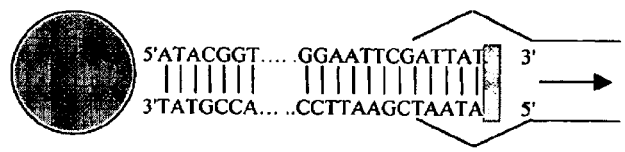

G) Once read, the DNA duplex is released from the nanopore by reversing the applied voltage. The cycle is then repeated at step B).

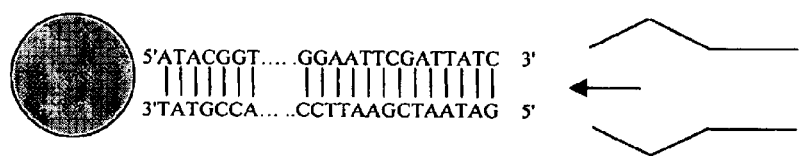

Figure 8

Table X. DNA hairpins used in this study. Primary sequence reads from 5' end at bottom left to 3' end at bottom right. Each hairpin has a 9 base-pair-long stem, and a four dT loop. The terminal base-pair and its nearest neighbor are highlighted by a box. These are the base-pairs in closest proximity to the pore limiting aperture when a given hairpin is captured in the α-hemolysin vestibule.

| SEQ ID NO:12 | SEQ ID NO:13 | SEQ ID NO:14 | SEQ ID NO:15 | SEQ ID NO:16 | SEQ ID NO:17 | SEQ ID NO:18 | SEQ ID NO:19 | SEQ ID NO:20 | SEQ ID NO:21 | SEQ ID NO:22 |
|---|---|---|---|---|---|---|---|---|---|---|
| T-T<br>T-T<br>G-C<br>C-G<br>A-T<br>G-C<br>C-G<br>T-A<br>T-A<br>G-C<br>5'  3' | T-T<br>T-T<br>G-C<br>C-G<br>A-T<br>G-C<br>C-G<br>T-A<br>T-A<br>C-G | T-T<br>T-T<br>G-C<br>C-G<br>A-T<br>G-C<br>C-G<br>T-A<br>T-A<br>A-T | T-T<br>T-T<br>G-C<br>C-G<br>A-T<br>G-C<br>C-G<br>T-A<br>T-A<br>T-A | T-T<br>T-T<br>G-C<br>C-G<br>A-T<br>G-C<br>C-G<br>T-A<br>T-A<br>T-G | T-T<br>T-T<br>G-C<br>C-G<br>A-T<br>G-C<br>C-G<br>T-A<br>T-A<br>T-T | T-T<br>T-T<br>G-C<br>C-G<br>A-T<br>G-C<br>C-G<br>T-A<br>T-A<br>F-A | T-T<br>T-T<br>G-C<br>C-G<br>A-T<br>G-C<br>C-G<br>T-A<br>A-T<br>G-C | T-T<br>T-T<br>G-C<br>C-G<br>A-T<br>G-C<br>C-G<br>T-A<br>A-T<br>C-G | T-T<br>T-T<br>G-C<br>C-G<br>A-T<br>G-C<br>C-G<br>T-A<br>A-T<br>A-T | T-T<br>T-T<br>G-C<br>C-G<br>A-T<br>G-C<br>C-G<br>T-A<br>A-T<br>T-A |
| 9bpGT/CA | 9bpCT/GA | 9bpAT/TA | 9bpTT/AA | 9bpTT/GA | 9bpTT/TA | 9bpFT/AA | 9bpGA/CT | 9bpCA/GT | 9bpAA/TT | 9bpTA/AT |

SEQUENCE LISTING

<160> NUMBER OF SEQ ID NOS: 22

<210> SEQ ID NO 1
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 1
ccgttttcgg                                                          10

<210> SEQ ID NO 2
<211> LENGTH: 12
<212> TYPE: DNA
<213> ORGANISM: Artificial Sequence
<220> FEATURE:
<223> OTHER INFORMATION: Synthetic oligonucleotide

```
<400> SEQUENCE: 2
cacgttttcg tg                                                      12

<210> SEQ ID NO 3
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 3
gaacgttttc gttc                                                    14

<210> SEQ ID NO 4
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 4
cgaacgtttt cgttcg                                                  16

<210> SEQ ID NO 5
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 5
ctgaacgttt tcgttcag                                                18

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
ctcgaacgtt ttcgttcgag                                              20

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 7
cttcgaacgt tttcgttcga ag                                           22

<210> SEQ ID NO 8
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 8
caacgtttcg ttg                                                     13

<210> SEQ ID NO 9
```

```
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 9
cgaacgtttt cgtacg                                                        16

<210> SEQ ID NO 10
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 10
tctgaacgtt ttcgttcag                                                     19

<210> SEQ ID NO 11
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 11
gaacgttttc gttcgaacgt tttcgttc                                           28

<210> SEQ ID NO 12
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 12
gttcgaacgt tttcgttcga ac                                                 22

<210> SEQ ID NO 13
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 13
cttcgaacgt tttcgttcga ag                                                 22

<210> SEQ ID NO 14
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 14
attcgaacgt tttcgttcga at                                                 22

<210> SEQ ID NO 15
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 15
```

```
tttcgaacgt tttcgttcga aa                                              22

<210> SEQ ID NO 16
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 16
tttcgaacgt tttcgttcga ag                                              22

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 17
tttcgaacgt tttcgttcga at                                              22

<210> SEQ ID NO 18
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)...(1)
<223> OTHER INFORMATION: N is difluorotoluene

<400> SEQUENCE: 18
nttcgaacgt tttcgttcga aa                                              22

<210> SEQ ID NO 19
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 19
gatcgaacgt tttcgttcga tc                                              22

<210> SEQ ID NO 20
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 20
catcgaacgt tttcgttcga tg                                              22

<210> SEQ ID NO 21
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 21
aatcgaacgt tttcgttcga tt                                              22
```

```
<210> SEQ ID NO 22
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 22
tatcgaacgt tttcgttcga ta                                              22
```

METHODS AND DEVICES FOR CHARACTERIZING DUPLEX NUCLEIC ACID MOLECULES

CROSS REFERENCE TO RELATED APPLICATIONS

Pursuant to 35 U.S.C. § 119 (e), this application claims priority to the filing date of the U.S. Provisional Patent Application Ser. No. 60/253,393 filed Nov. 27, 2000; the disclosures of which are herein incorporated by reference.

ACKNOWLEDGMENT

This invention was made with United States Government support under Contract No. 22401-443720, awarded by the Department of Energy; and Grant No. GH01826, awarded by the National Institutes of Health. The United States Government has certain rights in this invention.

INTRODUCTION

1. Field of the Invention

The field of this invention is nucleic acid characterization.

2. Background of the Invention

A variety of different protocols have been developed for characterizing nucleic acids. Such protocols include atomic force microscopy, video fluorescence microscopy, and force measuring laser tweezers. While the above protocols are available, there continues to be a need for the development of additional protocols for nucleic acid characterization. Of particular interest would be the development of a protocols and devices for performing the same which can resolve single nucleotide or single base-pair differences between otherwise identical duplex nucleic acid molecules, e.g., duplex DNA molecules, where the protocols would be rapid and capable of automation.

Relevant Literature

U.S. patent of interest include: U.S. Pat. Nos. 5,573,905; 5,723,598 and 6,015,714. In addition, see WO 00/28312. Also of interest are Akeson et al., Biophys. J (1999) 77:3227–3233; Wonderlin et al., Biophys. J. (1990) 58:289–297; and Kasianowicz, et al., Proc. Natl. Acad. Sci. USA (1996) 93: 13770–13773.

SUMMARY OF THE INVENTION

Methods and devices are provided for characterizing a duplex nucleic acid, e.g., a duplex DNA molecule. In the subject methods, a fluid conducting medium that includes a duplex nucleic acid molecule is contacted with a nanopore under the influence of an applied electric field and the resulting changes in current through the nanopore caused by the duplex nucleic acid molecule are monitored. The observed changes in current through the nanopore are then employed as a set of data values to characterize the duplex nucleic acid, where the set of data values may be employed in raw form or manipulated, e.g., into a current blockade profile. Also provided are nanopore devices for practicing the subject methods, where the subject nanopore devices are characterized by the presence of an algorithm that directs a processing means to employ monitored changes in current through a nanopore to characterize a duplex nucleic acid molecule responsible for the current changes. The subject methods and devices find use in a variety of applications, including, among other applications, the identification of an analyte duplex DNA molecule in a sample and the sequencing of duplex DNA molecules.

BRIEF DESCRIPTION OF THE FIGURES

FIGS. 6A to 6G provide a schematic of a protocol for nucleic acid sequencing employing the subject methods.

FIG. 8 provides Table 2 referenced in the experimental section, infra.

DESCRIPTION OF THE SPECIFIC EMBODIMENTS

Figure 1:
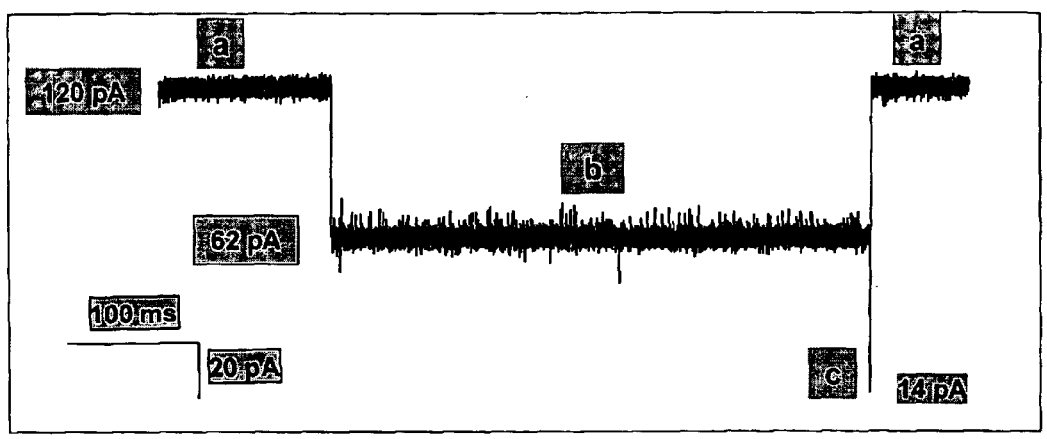
FIG. 1. Blockade of the α-hemolysin nanopore by a DNA hairpin. The figure shows a current trace caused by capture and translocation of a six base-pair DNA hairpin through the pore. a, The α-hemolysin heptamer inserted in a lipid bilayer. A 120 mV applied voltage across the open pore produces an ≅120 pA of ionic current in 1M KCl at room temperature. b, Capture of a six base-pair DNA hairpin in the channel causes an abrupt current reduction to an intermediate level ($I/I_o$=52% where I is the average event current and $I_o$ is the average open channel current). Because only linear single-stranded DNA can traverse the 1.5 nm limiting aperture, the stem duplex holds the molecule in the vestibule (760 ms median duration). The four deoxythymidines of the hairpin loop span the pore entrance, and the six base pairs of the stem extend into the vestibule. Note the increase in low frequency noise during hairpin occupancy of the vestibule relative to the open channel. c, Translocation of the DNA through the limiting aperture of the channel. The partial hairpin blockade ends with a sharp downward spike to approximately 14 pA ($I/I_o$=12%) that lasts about 60 $\mu$s. In our model, this corresponds to simultaneous dissociation of the six base pairs in the hairpin stem, which allows translocation of the extended strand. The event shown was digitally filtered at 10 kHz.

Methods and devices are provided for characterizing a duplex nucleic acid, e.g., a duplex DNA molecule. In the subject methods, a fluid conducting medium that includes a duplex nucleic acid molecule is contacted with a nanopore under the influence of an applied electric field and the resulting changes in current through the nanopore caused by the duplex nucleic acid molecule are monitored. The observed changes in current through the nanopore are then employed as a set of data values to characterize the duplex nucleic acid, where the set of data values may be employed in raw form or manipulated, e.g., into a current blockade profile. Also provided are nanopore devices for practicing the subject methods, where the subject nanopore devices are characterized by the presence of an algorithm that directs a processing means to employ monitored changes in current through a nanopore to characterize a duplex nucleic acid molecule responsible for the current changes. The subject methods and devices find use in a variety of applications, including, among other applications, the identification of an analyte duplex DNA molecule in a sample and the sequencing of duplex DNA molecules.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the subject components of the invention that are described in the publications, which components might be used in connection with the presently described invention.

Methods

As summarized above, the subject invention provides methods for characterizing double stranded, i.e., duplex nucleic acid molecules. By characterize is meant that the subject invention provides a method of assigning a unique description or signature to a duplex nucleic acid molecule, where the unique description/signature may subsequently be employed for a number of a different applications, as described in greater detail below. The unique description/signature provided by the subject methods is made up of nanopore current modulation data values generated by the duplex nucleic acid upon practice of the subject methods, i.e., one or more current based or derived identifying parameters or features which describe the affect of the duplex nucleic acid molecule on current through a nanopore under the influence of an applied electric field, as described more fully below. The signature assigned to a given duplex nucleic acid molecule by the subject methods may be made up of a collection or set of raw current modulation values or be made up of processed/manipulated current modulation values, e.g., a current blockade profile or portion/specific feature(s) thereof, e.g.,: shape of profile, duration, $I/I_o$, and the like.

The subject methods are capable of characterizing, i.e., assigning a unique identifying signature as described above, to a variety of types of duplex nucleic acids, including double-stranded DNA molecules, double-stranded RNA molecules, double-stranded nucleic acids that incorporate one or more synthetic or non-naturally occurring nucleotides, double-stranded RNA/DNA hybrids, etc. In many embodiments, the subject methods are employed to characterize double stranded DNA molecules, i.e., duplex DNA molecules.

The length of the duplex nucleic acid molecules that may be characterized according to the subject methods may vary from short duplex molecules ranging in length from about 2 to 50, usually from about 4 to 30 and more usually from about 4 to 20 bp in length, to much longer molecules, e.g., molecules that exceed 50, 100, 200, 1000, 2000, 5000, 10000 and even longer bp in length, including whole coding regions, whole genes, and even whole chromosomes. In many embodiments, the length of the duplex nucleic acid molecules that are characterized according to the subject methods range from about 3 to 100,000, usually from about 6 to 10,000 and more usually from about 6 to 1,000 bp.

A feature of the subject invention is that a nanopore device is employed to characterize the duplex nucleic acid, i.e., assign a unique identifying signature based on measured modulations in current through a nanopore. Specifically, the duplex nucleic acid is contacted with a nanopore present in a device under the influence of an applied electric field and the effect over time on a measurable signal through the nanopore is observed and employed to characterize or assign an identifying signature to the duplex nucleic acid, where the signature may take a number of different forms, e.g., a collection of raw data values, a manipulated set of data values such as is found in a current blockade profile, and the like.

The nanopore device that is employed in the subject methods is typically a device that comprises a nanopore inserted into a thin film with means for applying an electric field across the nanopore and for measuring the resultant signal at the nanopore. By nanopore is meant a structure having a channel or pore with a diameter of "nano" dimensions, where the inner diameter of the pore or channel typically ranges from about 1 to 10, usually from about 1 to 5 and more usually from about 1 to 2 nm. The nanopore may be synthetic or naturally occurring, where naturally occurring nanopores include oligomeric protein channels, such as porins, gramicidins, and synthetic peptides and the like, where a particularly preferred protein channel is the self-assembled heptameric channel of α-hemolysin. In one embodiment, the thin film into which the nanopore is inserted is a lipid bilayer fabricated from a wide variety of one or more different lipids, where suitable lipids include: phosphatidlycholine, phosphatidylserine, phosphatidylethanolamine, glycerol mono-oleate, and cholesterol.

A variety of suitable thin film support devices have been reported in the literature that may be used to support the nanopore used to detect the molecular bar code. Such devices include those described in: Brutyan et al., Biochimica et Biophysica Acta (1995) 1236:339–344; Wonderlin et al., Biophys. J. (1990) 58:289–297; Suarez-Isla et al. Biochemistry (1983) 22:2319–2323 as well as those disclosed and reviewed in U.S. Pat. No. 6,015,714; the disclosure of which is herein incorporated by reference.

Of particular interest is the device described in WO 00/28312 and its corresponding U.S. application Ser. No. 09/430,240, the disclosure of which is herein incorporated by reference. In these embodiments, the subject single-channel thin film devices include the following elements: (a)

a cis chamber; (b) a trans chamber; (c) an electrical communication means connecting the cis and trans chambers; and (d) a thin film at the cis terminus of the electrical communication means that contains a single nanopore or channel.

The cis and trans chambers may have any convenient configuration. As such, the cis and trans chambers may have a conical, cylindrical, cube, or other shape as desired. The volume of the chambers may vary as well, where the volume of each chamber is at least about 1 $\mu$l, usually at least about 10 $\mu$l and more usually at least about 50 $\mu$l, and may be as large as 1 ml or larger, but will usually not exceed about 2 ml and more usually will not exceed about 10 ml. In certain preferred embodiments, e.g. where microgram quantities of nucleic acid are analyzed, as described in greater detail below, the chambers will have relatively small volumes, ranging from about 1 $\mu$l to 10 $\mu$l and usually from about 10 $\mu$l to 50 $\mu$l. The shape and volume of the cis and trans chambers may be the same or different, such that the shape or volume of the cis chamber may be substantially similar to that of the trans chamber or different from that of the trans chamber.

Connecting the cis and trans chambers is an electrical communication means. By electrical communications means is meant a conduit or vessel that is capable of holding a conductor through which an electrical current can flow, e.g. an electrolyte solution. In a typical application, the conduit or vessel has an opening in the cis chamber and the trans chamber, i.e. it has an open cis end and an open trans end, thereby allowing for fluid flow and, importantly, ionic current flow under appropriate conditions, e.g., an applied electric field. The conduit or vessel may have a variety of different cross-sectional shapes, where various cross-sectional shapes of interest include circular, square, oval, rectangular, trapezoidal, and the like. In general, the average cross-sectional area along the entire electrical communication means will be at least about 10 $\mu$m$^2$, usually at least about 50 $\mu$m$^2$ and more usually at least about 500 $\mu$m$^2$, where the cross-sectional area may be as large as 2 mm$^2$ or larger, but will usually not exceed about 1 mm$^2$ and more usually will not exceed about 0.6 mm$^2$. In preferred embodiments, the electrical communication means is a tubular structure that has a circular cross-sectional shape along its entire length. In these preferred embodiments, the average diameter along the entire length of the electrical communication means is at least about 10 $\mu$m, usually at least about 50 $\mu$m and more usually at least about 500 $\mu$m, where the diameter may be a large as 2 mm or larger, but will generally not exceed about 1 mm and usually will not exceed about 0.8 mm. At least the cis end of the electrical communication means enters the cis chamber through the floor or wall of the cis chamber. The cis end may be flush with the floor or wall of the cis chamber or extend a small distance into the cis chamber, where that distance will not exceed about 2 mm and usually will not exceed about 1 mm. In many embodiments, the trans end will be associated with the trans chamber in an analogous fashion. In such embodiments, the electrical communication means generally is the shape of a "U," e.g. where the electrical communication means is a U-shaped patch tube filled with an electrolyte solution. The length of the electrical communication means typically ranges from about 0.5 mm to 5 mm, usually from about 1 mm to 4 mm and more usually from about 2 mm to 3 mm.

At the cis end of the electrical communication means is a conical aperture (or opening) of $\mu$m dimensions, e.g. a conical fitting or cap with a $\mu$m sized opening. In other words, the cis end of the electrical communication means has an internal conical bore with a hole at the end. As the aperture or opening is of $\mu$m dimensions, it typically has a diameter ranging from about 1 to 100 $\mu$m, usually from about 5 to 50 $\mu$m and more usually from about 10 to 25 $\mu$m. The cis end of the electrical communication means may be fabricated such that it gradually narrows at the cis end to provide for a conical aperture of $\mu$m dimensions (i.e. the conical aperture may be part of the electrical communication means), or the cis end may be capped with a separate conical aperture component or element that fits over or caps the cis end or terminus. In a preferred embodiment, the opening of the conical aperture at the cis end is horizontal, i.e. it is parallel to the water line of fluid, when present, in the cis chamber and the horizon of the substrate on which the device rests.

The horizontal aperture at the cis end of the electrical communication means is sealed with a thin film, such as a lipid bilayer. A variety of different lipid bilayers are known in the art and may be used to produce the thin film and seal the horizontal cis conical aperture. Representative lipid bilayers included those prepared from one or more lipids of the following group: phosphatidylcholine, phosphatidylserine, phosphatidylethanolamine, glycerol mono-oleate, cholesterol, etc. The thin film may also be formed by inorganic materials such as silicon nitride, and the like.

Inserted into the horizontal bilayer is a single channel or nanopore through which ionic current can flow, e.g. from the cis to the trans side of the pore upon application of an applied electric field. As used herein, the terms "nanopore" and "channel" are used interachangeably to refer to structures having a nanoscale passageway through which ionic current can flow. The inner diameter of the nanopore may vary considerably depending on the intended use of the device. Typically, the channel or nanopore will have an inner diameter of at least about 0.5 mn, usually at least about 1 nm and more usually at least about 1.5 nm, where the diameter may be as great as 50 nm or longer, but in many embodiments will not exceed about 10 nm, and usually will not exceed about 2 nm.

The nanopore should allow a sufficiently large ionic current under an applied electric field to provide for adequate measurement of current fluctuations. As such, under an applied electric field of 120 mV in the presence of pH 7.5 buffered solution (as described in the experimental section, infra), the open (i.e. unobstructed) nanopore should provide for an ionic current that is at least about 1 pA, usually at least about 10 pA and more usually at least about 100 pA. Typically, the ionic current under these conditions will not exceed about 0.5 nA and more usually will not exceed about 1 nA. In addition, the channel should provide for a stable ionic current over a relatively long period of time. Generally, channels finding use in the subject devices provide for accurate measurement of ionic current for at least about 1 min, usually at least about 10 min and more usually at least about 1 hour, where they may provide for a stable current for as long as 24 hours or longer.

The single nanopore that is inserted into the lipid bilayer may be a naturally occurring or synthetic nanopore. Typically the nanopore will be a proteinaceous material, by which is meant that it is made up of one or more, usually a plurality, of different proteins associated with each other to produce a channel having an inner diameter of appropriate dimensions, as described above. Suitable channels or nanopores include porins, gramicidins, and synthetic peptides. Of particular interest is the heptameric nanopore or channel produced from α-hemolysin, particularly α-hemolysin from *Staphylococcus aureus*, where the channel is preferably rectified, by which is meant that the amplitude of the current flowing in one direction through the channel exceeds the amplitude of the current flowing through the channel in the opposite direction.

The single-channel thin films of the device are configured so as to provide for high resistance, low noise and stability. As such, the resistance of the subject single-channel bilayers is at least about 1 gigaohm, usually at least about 10 gigaohm and more usually at least about 200 gigaohm, where the resistance may be as high as 500 gigaohm or higher. The noise preferably does not exceed about 0.6 pA and usually does not exceed about 0.5 pA RMS at 5 kHz bandwidth in whole cell mode, and does not exceed about 0.4 pA and usually does not exceed about 0.2 pA RMS in patch mode. Furthermore, the subject single channel bilayers are stable for period of at least about 1 min, usually at least about 1 hour under an applied electric field of 100 mV or more, where the subject bilayers may be stable for much longer periods under the same conditions, e.g. they may be stable for periods of 24 hoursor longer. In addition, the capacitance of the bilayer ranges from about 0.3 to 1.5 $\mu F$ $cm^{-2}$, usually from about 0.4 to 1.2 $\mu F$ $cm^{-2}$ and more usually from about 0.3to 0.4 $\mu F$ $cm^{-2}$.

The subject devices also generally comprise a means for applying an electric field between the cis and trans chambers, and therefore between the cis and trans sides of the bilayer and single nanopore present therein. The electric field applying means is typically capable of generating a voltage of at least about 10 mV, usually at least about 50 mV and more usually at least about 100 mV. Typically, the electric field generating means is made up of silver chloride electrodes positioned in the cis and trans chambers that are connected to a voltage source.

The device typically further comprises a means for monitoring the current flow through the channel and processing the observed current flow to produce a usable output. Generally, such monitoring means includes a very low noise amplifier and current injector, and an analog to digital (A/D) converter. The device may further comprise other elements of the output generating system, including data acquisition software, an electronic storage medium, etc. A suitable system is described in the experimental section, infra.

The cis and trans chambers may be fabricated from a wide variety of materials. Typically these components will be fabricated or at least lined with a relatively inert material, such as a polymeric material, e.g. Teflon. The components may be fabricated using any convenient technique, e.g. machining.

In characterizing the duplex nucleic acid with a nanopore device, the first step is to place the to be characterized duplex nucleic acid on the cis side of the nanopore, e.g., by placing a fluid conducting medium that includes the target duplex nucleic acid, such as an aqueous fluid sample that includes the target duplex nucleic acid, on the cis side of the nanopore. The duplex nucleic acid will generally be in an aqueous solution, e.g. a buffered solution, where the solution typically comprises one or more dissolved salts, such as potassium chloride and the like, and the pH ranges from about 6.0 to 9.0, and more usually from about 7.0 to 8.5. The solution on the trans side of the nanopore may be the same or different from the solution on the cis side, but will also generally be an ionic buffered solution.

After the duplex nucleic acid is placed on the cis side of the pore, a voltage is applied across the pore, conveniently by electrodes positioned in the cis and trans side of the pore. The voltage that is applied is sufficient to cause the duplex nucleic acid to enter the opening or vestibule of the nanopore, and may range from about 60 to 260 millivolts, usually from about 80 to 200 millivolts and more usually from about 100 to 160 millivolts.

Depending on the nature of the target duplex nucleic acid molecule, the electric field may be applied in a constant or pulsed fashion. For example, with shorter duplex nucleic acid molecules, the electric field may be applied in a constant fashion. By shorter is meant molecules that do not exceed about 8 bp, usually do not exceed about 7 bp and more usually do not exceed about 6 bp in length. By constant is meant that the direction of the applied electric field is not changed during practice of the subject method.

Figure 15:
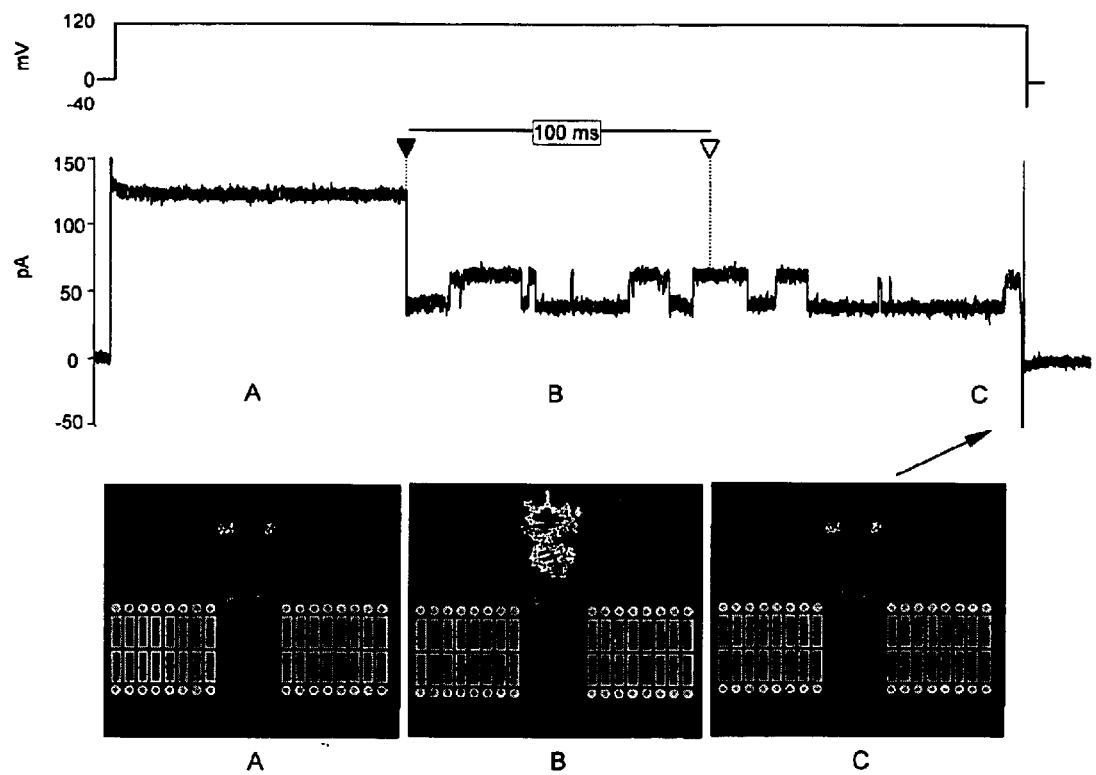
FIG. 15. Examination of DNA duplex ends using a voltage-pulse routine. The upper trace represents the voltage across the pore which begins at 0 mV. Applying 120 mV (trans side positive) results in a current increase to 120 pA through the open a-hemolysin channel (A in the lower trace and in the corresponding diagram). With time, duplex DNA is pulled into the pore by the potential causing an abrupt current decrease (B). After 300 ms, the potential is reversed (−40 mV, trans side), clearing the pore (C). The cycle is then repeated to examine the next molecule. The dashed lines at the filled and at the open arrows in the lower trace denote the beginning and the end of a 100 ms window that is used to identify each blockade signature. In the diagrams, the stick figure in blue is a two dimensional section of the a-hemolysin pore derived from X-ray crystallographic data (Song et. al.). A ring of lysines that circumscribe a 1.5-nm-limiting aperture of the channel pore is highlighted in red. A ring of threonines that circumscribe the narrowest, 2.3-nm-diameter section of the pore mouth is highlighted in green. In our working model, the four dT hairpin loop (yellow) is perched on this narrow ring of threonines, suspending the duplex stem in the pore vestibule. The terminal base-pair (brown) dangles near the limiting aperture. The structure of the 9bp hairpin shown here was rendered to scale using WebLab ViewerPro.

For longer duplex nucleic acids, it is preferable to employ a pulsed applied electric field. By pulsed electric field is meant an electric field that changes, e.g., reverses, direction at least once during the practice of the subject methods. By longer is meant a duplex nucleic acid that is at least about 6 bp, usually at least about 7 bp and more usually at least about 8 bp in length. In these embodiments, the pulsed electric field is generally applied to the fluid medium in a manner sufficient such that the duplex nucleic acid is not translocated through the nanopore to the other side of the nanopore. In other words, the electric field is applied in a manner such that the entire duplex nucleic acid does not pass through the nanopore from one side to the other under the influence of the applied electric field. Typically, the pulsed electric field is applied in a first direction, conveniently referred to as the forward direction, and is then applied in a second direction, conveniently referred to as the reverse direction, where the switch from the forward to reverse direction occurs prior to translocation of the duplex nucleic acid through the nanopore, as described above. In many embodiments, the forward electric field is maintained for a period of time that is longer than the reverse direction, where the difference may be 2, 5, 10 fold or longer. In many embodiments, the duration of the applied forward electric field ranges from about 10 milliseconds to 10 seconds, usually from about 100 milliseconds to 1 second, while the duration of the applied reverse electric field ranges from about 10 microseconds to 10 milliseconds, usually from about 100 microseconds to 1 millisecond. See e.g., FIG. 15.

As explained above, the subject methods characterize duplex nucleic acids based on observed modulations/changes in current flow through a nanopore resulting from contact of the nanopore with the duplex nucleic acid. As such, during application of the applied electric field, the ion current through the nanopore is measured or monitored over a period of time. Measurements are typically made at least every 1 s, usually at least every 0.1 s and more usually at least every 0.01 s using a single nanopore. This step results in the production of a set of measured current derived data files, where the set typically consists of at least about 5, usually at least about 10 and more usually at least about 50 individual measured data points, where the set generally includes many more data points, usually at least about 100, 1000, 5000 or more. Because each duplex nucleic acid gives rise to a unique set of current derived data points upon contact with the nanopore under the influence of the applied electric field, the resultant set of data points can be used to characterize that nucleic acid molecule and distinguish it from any other nucleic acid molecule which differs from it in terms of even one base/base pair, at least with respect to the end which contacts the nanopore during practice of the subject methods. In other words, the resultant set of data points can be used to assign an identifying signature to the duplex nucleic acid molecule, as described above. As mentioned above, the resultant measured data values may be employed in raw form but are conveniently manipulated to provide for increased ease of use. For example, in many embodiments, the measured data values are then manipulated to produce a current blockade profile or similar output capable of being employed to characterize the duplex nucleic acid, i.e. as an identifying signature for the duplex nucleic acid.

As demonstrated by the above description, the subject methods provide a means for characterizing, i.e., assigning a signature, to individual duplex nucleic acid molecules. As such, the subject methods find use in a variety of applications in which it is desired to characterize a duplex DNA molecule. Different representative applications in which the subject methods find use are now reviewed.

The subject methods can be employed in distinguishing different nucleic acids from each other, even if the nucleic acids differ from each other by a single nucleotide/base pair. Thus, the subject methods may be employed to sort mixtures of nucleic acids, where the sorting protocol may or may not require the use of a pulsed electric field depending on the nature of the duplex nucleic acids in the mixture.

Another application in which the subject invention finds use is in the identification of the presence of an analyte duplex nucleic acid of interest in sample, where the sample may include two or more distinct nucleic acid molecules which differ from each other by sequence, where such a mixture may have 10, 50, 100, 1000 or more distinct duplex nucleic acids. As such, the subject methods find use in applications where two or more duplex nucleic acids are distinguished from one another, as well as duplex nucleic acid analyte detection assays in which the duplex nucleic acid analyte is present in a complex mixture or sample, which complex mixture or sample may further include one or more additional non-analyte duplex nucleic acids from which the target analyte must be distinguished.

In these types of duplex nucleic acid detection applications, the sample suspected of including the duplex nucleic acid analyte is contacted with the nanopore as described above and a set of measured data values is obtained and employed to assign a signature to the duplex nucleic acid, as described above. The observed signature is then screened against a reference signature of collection of reference signatures to assign an identity to the observed signature. If the observed signature matches the reference signature, the measured sample is determined to include the analyte duplex nucleic acid having the reference signature, i.e., the presence of the analyte duplex nucleic acid in the sample being assayed is positively identified. The presence of a single analyte duplex nucleic acid or a plurality of different analyte duplex nucleic acids may be assayed using the above protocol.

Specific instances where the above methods of analyte nucleic acid detection in a sample find use is in the detection of nucleic acid analytes which are derived from pathogens, in the detection of the presence of single nucleotide polymorphisms in a sample of nucleic acids, and the like.

Yet another application in which the subject methods find use is in the in vitro detection of DNA damage (e.g. depurination and thymine dimerization). In this specific application, the signature of a damaged duplex DNA molecule is employed as the reference signature against which an observed signature obtained from a sample suspected of having the damaged DNA molecule of interest is screened, as described above. A positive correlation between the observed and referenced signatures indicates the presence of the damage DNA of interest in the sample.

Figure 2:
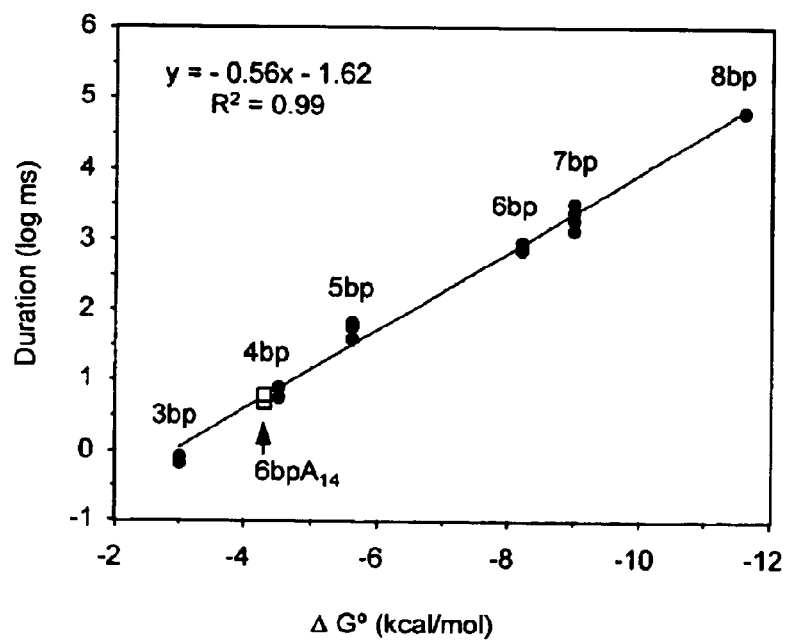
FIG. 2. Standard free energy of hairpin formation vs shoulder blockade duration. Standard free energy of hairpin formation was calculated using the mfold DNA server (see Table 1), and correlated with median duration of hairpin shoulder blockades (solid circles). Each point represents the median blockade duration for a given hairpin length acquired using a separate α-hemolysin pore on a separate day. Median blockade durations and $\Delta G°$ for the equivalent of the 6 bp hairpin with a single mismatch (6bpA$_{14}$, Table 1) are represented by open squares. All experiments were conducted in 1.0 M KCl at 22±1° C. with a 120 mV applied potential.

Yet another application in which the subject methods find use is in the measurement of duplex stability changes caused by nucleotide modifications or by binding of other solutes to the DNA. In this application, a standard curve is established showing the relationship between blockade duration and $\Delta G°$ of formation for DNA hairpins of known sequence under specified conditions such as temperature and salt concentration. An example is shown in FIG. 2. An experimental hairpin is then introduced in which one or more nucleotides is modified. Blockade duration for a population of those experimental hairpins may then be compared with the standard curve. This analysis results in a quantitative measure of the effect of the nucleotide modification on duplex stability.

Yet another application in which the subject methods find use is in the measurement of enzyme kinetics. For example, a target DNA duplex may be added to a solution adjacent to the nanopore. This duplex is captured and examined repeatedly by the nanopore, establishing a control signature. An enzyme that modifies or binds to the DNA is then added to the system (e.g. kinases, exonucleases, endonucleases, methylases), and the change in the blockade signature is monitored as a function of time. The resultant data is then employed for determination of enzyme kinetics.

The subject methods also find use in DNA sequence analysis, i.e. the determination of the sequence of at least a portion of, if not an entire, duplex DNA molecule. In such applications, a fluid conducting medium that includes the duplex DNA molecule to sequenced is obtained. The duplex DNA molecule to be sequenced is protected at one end, e.g., the 3' or 5' end, by a group or feature that is capable of protecting the end from enzymatic degradation/attack, e.g., by the presence of a protecting group, through attachment to a solid support, etc. The other end of the duplex molecule to be sequenced is blunt-ended, where the other end may be rendered blunt ended by contact with an appropriate enzymatic activity, e.g., mung bean nucleases, S1 nuclease and the like. In these applications, the first step is to modify the blunt ended molecule to produce a single nucleotide overhang at the former blunt end. This step is generally performed by contacting the nucleic acid with an appropriate enzymatic activity that is capable of acting on a blunt ended nucleic acid and removing a single nucleotide to produce a single nucleotide overhang at the former blunt end. Examples of suitable enzymatic activities for this step of the subject methods include: exonuclease III and the like. Following production of the single nucleotide overhang, the fluid medium is then subjected to a pulsed electric field as described above and the resultant characterization signature, e.g., current blockade profile, is recorded. Following this step, the single nucleotide overhang is converted to a blunt end. This step is conveniently accomplished using an enzyme that converts an overhang end of a nucleic acid molecule into a blunt end. Optionally, the blunt ended molecule may then be contacted with the nanopore to obtain a current blockade profile or other identifying characterization signature for the blunt end. The resultant blunt ended molecule is then contacted with an enzyme or other agent to produce a single nucleotide overhang. This second overhang comprising molecule is then contacted with the nanopore to obtain a current blockade profile or other characterizing signature for this second overhang molecule. The above steps are repeated a plurality of times to obtain a series of current blockade profiles or characterizing signatures for each different overhang and optionally blunt ended molecule that is produced by the sequential removal of a single nucleotide from the end of the molecule being analyzed. In most embodiments, enzymes are eluted from the system between each step in DNA modification, however under appropriate conditions cutting that yields overhangs and blunt ends may be synchronized without elution and re-addition of enzymes. Finally, the nucleotide sequence of the molecule being analyzed may be deduced from the resultant collection of current blockade profiles or other characterization signatures, e.g., through appropriate comparison with a reference collection of characterization signatures. By knowing the order in which each signature is observed and the particular sequence configuration at the end of the molecule to which the signature corresponds, one can readily deduce the nucleotide sequence of the DNA molecule. The above protocol is schematically represented in FIGS. 6A to 6G.

The subject methods also find use in analysis of single nucleotide polymorphisms (SNPs). For example, an array of oligonucleotide 21 mers is fabricated wherein each oligonucleotide is equivalent to sequence in native DNA at an SNP. Another set of oligonucleotide 20 mers is synthesized each of which is the reverse complement to an oligonucleotide in the array minus one base at its 3' end where the SNP is known to occur. This latter set is annealed to the target DNA and extended by one nucleotide using a DNA polymerase and ddNTPs as substrate. The extended oligomers are recovered (e.g. by biotinylated 5' ends) and annealed to the array. A nanopore (or array of nanopores) then reads the product at each position in the array. Double-stranded DNA can be distinguished from single-stranded DNA at each position in the array, and the identity of each pair of bases at the terminus can also be identified by the nanopore. This process specifically identifies the base at each SNP that was examined.

Automated Data Interpretation

As mentioned above, the data sets that result from practice of the subject methods and are employed to characterize duplex nucleic acids according to the subject methods may be interpreted without the aid of a computing means, i.e. manually. However, in most embodiments of the subject methods, the data interpretation step is, at least in part, performed by an automated data interpretation or processing means, i.e., computing means, which is typically made up of hardware and software computing means, where the computing means typically includes an algorithm that is capable of at least directing the steps required to characterize a duplex nucleic acid according to the subject invention, e.g., to process the raw observed current modulation data into a signature in the form of a current blockade profile. The algorithm may further be capable of comparing an observed signature to one or more reference signatures to further identify the nucleic acid giving rise to the observed signature, e.g., to determine the length of the duplex nucleic acid, to determine the identity of duplex nucleic acid, to sort or otherwise distinguish two different nucleic acids that may differ by as little as one nucleotide/base pair, etc. A representative algorithm is the FSA/SVM algorithm described in detail in the Experimental Section below. The algorithm may further be capable of determining the sequence of a nucleic acid by automatically performing the steps described above in terms of sequencing nucleic acids with the subject methods. When employed, the algorithm may be an integral part of the hardware of the device or may be present in a software component which interacts with the hardware component of the device to perform the desired data interpretation and processing, as described above. Details of the automated data acqustion and analysis procedure are described below.

Signal Acquisition

The FSA used for signal acquisition is based on a fast, single-pass, time-domain evaluation of blockade reductions. Those blockades satisfying a set of FSA constraints are acquired as candidate signals. The FSA uses signal substates that can be interpreted as signal "starts", "ends", and "interior." Good signal acquisition is achieved with constraints on valid "starts" that are weak (with prominent use of "OR" conjugation) and constraints on valid "ends" that are strong (with prominent use of "AND" conjugation). When used with very strict conditions for valid "interior," a highly accurate signal recognition automaton can result for that type of training data. The statistical measures of SN and SP on the signal acquisitions in this data analysis are better than 99.99% when the various constraints are properly tuned. Also, the identification of signal "starts" and "ends" typically falls within one sample point (5 $\mu$sec) of the inflection points of the start and end blockade transitions (which is far more precision than is necessary for the analysis that follows). The speed of the FSA "scan" is comparable to performing a simple binary-to-ASCII conversion.

If the FSA tunings for the different training sets led to FSAs that only acquired signals for which they were optimized, the individual SN=99.99%=SP results would extend to the overall signal identification/discrimination problem. Such a solution, solely in terms of the FSA, would have to contend with two difficulties in order to be scalable: scalable tuning and scalable, disjoint, signal acquisition. While scalable tuning is conceivable, via automation of the tuning methods that will be described for obtaining the generic signal acquisition, the possibility of scalable, disjoint, signal acquisition is remote. (For a sufficiently small set of signal types, however, and making allowances for dropping "weak" data, a solely FSA based assayer could be constructed, and it would be very fast computationally.) The role of the FSA in the analysis that follows is, thus, restricted to a single choice of tuning that provides generic signal recognition. Tuning for generic signal acquisition is accomplished by maintaining the sensitivity on the acquisitions at SN=99.99%, while the specificity (for a given type of molecule) is relaxed to whatever extent necessary.

Tuning for the FSA for generic signal acquisition is accomplished by relaxing various constraints and measuring the counts on observed signals. One such constraint is the baseline normalized current blockade (I/Io) required to transition to the sub-signal "start" state. By relaxing this constraint a maximum signal count is eventually achieved, and that is the constraint setting chosen for generic signal acquisition. (The fall-off in signal count arises from false triggers on signal "starts," due to baseline noise, that masks the true signal starts.) Another constraint relates to the lower bound on I/Io for the baseline following a return-to-baseline sub-signal "end" state. Constraint relaxation may be performed until the specificity rapidly degrades (due to false signal acquisition from baseline noise).

As candidate signals are acquired their start and end positions within the data file are recorded, along with simple statistics such as blockade duration, average I/Io, standard deviation of I/Io, minimum I/Io in signal interior, and maximum I/Io in signal interior. It is possible to choose small sets (<10) of molecules such that highly accurate discrimination is directly possible in terms of simple statistics, particularly if the blockade durations of the molecules span several magnitudes, as with the hairpin molecules. The sensitivity needed for SNP recognition and DNA sequencing, however, requires much more extensive characterization of the signals and this is accomplished by means of wavelet quantization of the signal at the next stage of processing.

Signal Feature Extraction

At the second stage of processing, the candidate signals acquired by the (time-domain) FSA are re-analyzed by a new FSA based on local wavelet characteristics of the signal. The local wavelet features are defined in terms of the local sum and difference coefficients of a Haar Wavelet Transform. The coefficients for the $n^{th}$ order sums correspond to a $2^n$ length moving average, while the coefficients for the $n^{th}$ order differences are a "moving" version of the conventional wavelet coefficients of that order. An efficient generalization of the In-place Fast Haar wavelet Transform to a "moving" transform is used to obtain the "locally" defined coefficients mentioned above. In particular, the characterization of the local time-domain sampling of the signal is decomposed in terms of the wavelet transform with origin at that local time sampling. Once a local notion of signal average and signal "difference" is obtained the mapping to a local sub-signal state is performed.

The wavelet-domain FSA uses a specified set of quantization states. The quantization maps the time-domain sequence to a finite selection of sub-signal states associated with the wavelet-domain sequence. The wavelet order is chosen (tuned) such that the sequence of sub-signal states corresponding to a given signal region will form a stable "grammar" of states for that signal. To provide an example of this, consider a simplified set of sub-signal states denoted by "B" for baseline, "T" for transition, "S" for shoulder or spike (the low difference wavelet part of the spike region is merely considered as a second shoulder region). With such a set of states, a typical signal, should be labeled like so:

"----
BBBBBTTTTTSSSSSSSSSSSSSSSSSSSSSSSSSSSTTTTTSSS-TTTTTTTBBBBBBBBB---"

For the quantization used in this paper, the baseline states are defined to have sum coefficient greater that 83% of baseline current while their difference coefficient is less than 8.3% of baseline current. The transition states have difference coefficient greater than 8.3%, and the shoulder/spike states have sum coefficient less than 83% of baseline current with restriction on difference coefficient like that of the baseline states. If the order that defines the wavelet sum and difference coefficients is too low, the above labeling will typically "fail" by becoming too sensitive to fluctuations in the difference coefficients:

"----BTBT-
BTTTTTSSTSSSTSSSTTSSSSSTTSSSTSSSTTTTTSSSTTTT-TTTBBTBBTBBB---"

Since each increment in the wavelet order doubles the computational demands, the smallest wavelet order that provides a stable "grammar" of {B,T,S} labelings is chosen so as to incur the least computational expense. For the data considered in this paper (with 5 $\mu$sec sampling), the smallest wavelet order for stability is at found at fifth order. Tuning wavelet order for a stable grammar is sensitive to the noise characteristics of the signal group.

The wavelet-domain FSA is based on an elaboration of the sub-signal states described above, where states are sub-indexed by the sum wavelet and difference wavelet strengths. In the analysis done here, the resolution on the quantization of sum wavelets is chosen to be in 1% increments of Io (baseline current), while the resolution on the difference wavelet quantization is in 2% increments of Io. Although it is possible for the wavelet-domain FSA to perform the initial signal acquisition in its own right, it is found that the demarcation of signal "start" and "end" values is much less accurate than that of the time-domain FSA. When coupled with the fact that the simple time-domain FSA scans at about a magnitude greater speed than the wavelet-domain FSA (when operating on a fifth order wavelet basis), it is clear that signal "cutouts" should be left to the time-domain FSA. A role for the wavelet-domain FSA as signal verifier is still reasonable, however, since the time-domain FSA information can direct the wavelet-domain FSA to regions where candidate signals reside, and this is done in the analysis. When operating in its signal verification role, the wavelet-domain FSA also provides a means to exclude signals that are non-diagnostic, an example of such being spike durations greater than shoulder durations. The number of signals dropped as non-diagnostic is typically less than 5%, and this greatly aids the SVM discrimination since the non-diagnostic signals for the different molecules are usually full blockades or "stuck" modes that the molecules have in common.

Figure 7:
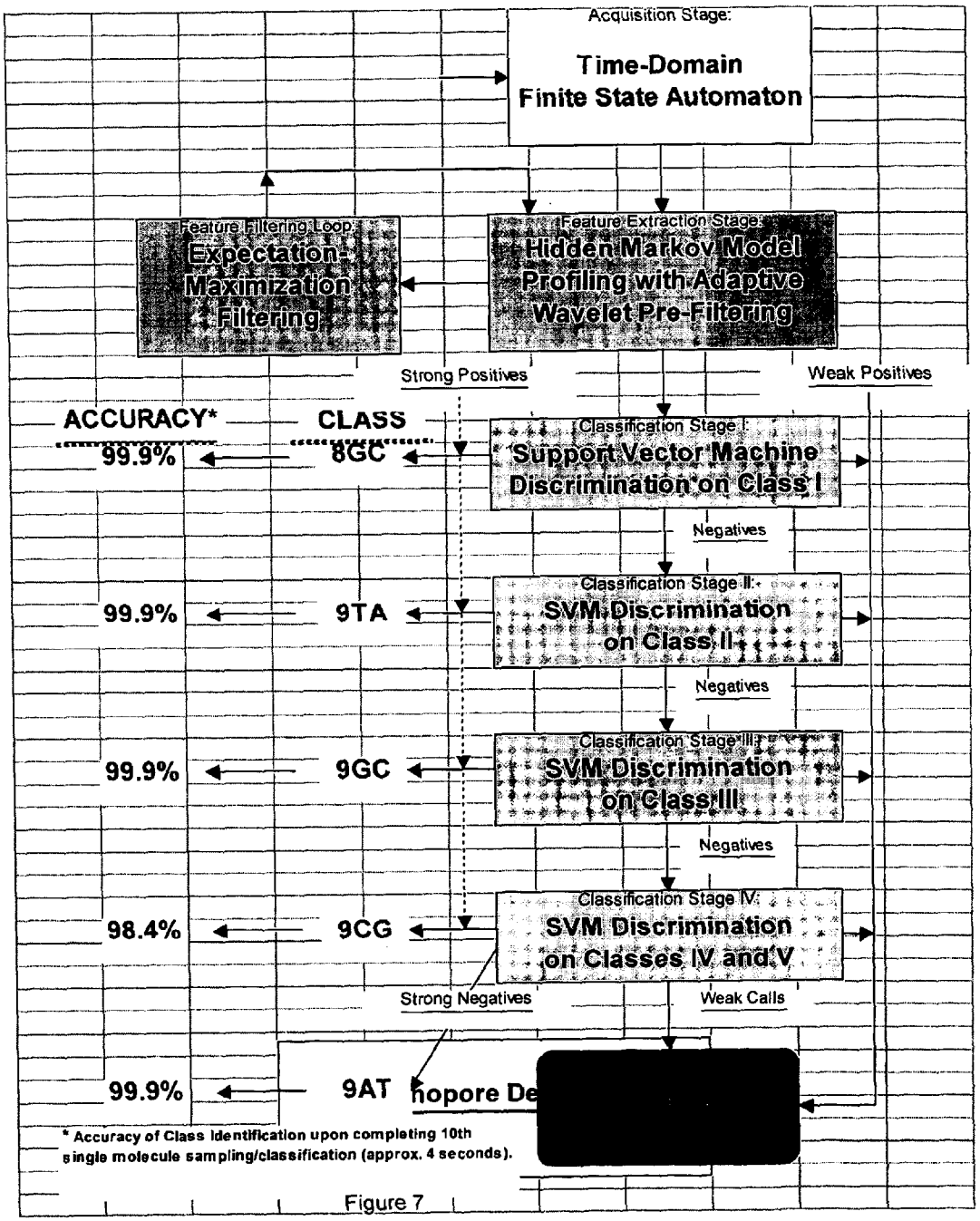
FIG. 7 provides the Feature Extraction Stage and Feature Filter Loop of the HHM analysis that may be employed in the subject invention.

The choice of wavelet quantization states (including specification of order on the underlying wavelets) can be optimized using Hidden Markov Models (HHM). The HMM processing is based on fifty states, corresponding to current blockades that range from 20% residual current to 69% residual current (with states separated by 1% increments). Signal blockades (of duration 100 msec or greater) that fall outside this range are rare and generally non-diagnostic and are dropped by the HMM. Signal not rejected by the HMM is then filtered by Expectation/Maximization (EM), with five feedback cycles, to filter the set of HMM parameters from which the feature vectors are derived (the Feature Extraction Stage and Feature Filter Loop are shown in FIG. 7). The feature vector consists of 150 components. The first 50 feature components describe the blockade probability for each of the 50 HMM states and they are obtained using the HMMs emission coefficients together with prior estimation using the a posteriori distribution on states (indicated by sampling along the HMMs Viterbi path). The second set of 50 components corresponds to parameterization of the HMM emission coefficients as Gaussians, with mean fixed by the blockade level they are meant to describe. Thus, evaluations of the emission "spread," via the variance, define the second set of 50 components, with one variance parameter per emission from a given state. The third, and last, set of 50 components correspond to a compression on the transition parameter information of the HMM. The compression is based on the selection indicated by the two highest probability blockade levels (that are restricted to be local maxima, e.g., the bi-levels). The transition coefficients from the two indicated levels are combined with weighting the probability of the associated blockade level. With such a compression on the transition data, a 50 component encapsulation of the distinctive bi-level toggling between major levels is obtained, and that completes the 150 component feature vector.

Such optimization is not conveniently scalable when considering sub-sets of the signals, not to mention large numbers of signal types, so is not used in what follows. The HMM framework, however, provides some insight as to the choice of feature set (from the perspective of a generative FSA model on stochastic sequential channel sequence) that would also be useful for later discriminative modeling (by Support Vector Machine). In the HMM framework, one feature set that could be chosen is motivated by the Fisher Score, which is defined relative to the optimized HMM representation for a channel signal 'X'. The Fisher Score, 'Z,' is the gradient of the log-likelihood score for channel signal X, with components the derivatives with respect to the HMM's state and transition probabilities '$\theta$':

$$Z_\theta(X) = \nabla_\theta \log P(X|\theta).$$

Since the log function is a monotonically increasing function, the magnitude of a Fisher Score component provides a comparative indicator as to the role of that component in the log-likelihood evaluation on X. If normalized to one, the Fisher Score components approximately describe frequencies of usage on the state and transition probabilities 'θ' in the HMM estimation of X. The frequency of the states and transitions used in the HMM estimation of 'X' are, thus, indicated as the approximate feature vector components to pass to the SVM. In terms of the generative model that employs a FSA instead of an HMM, such a choice of feature vector, in terms of a decomposition of state frequencies, is what is used.

Once the wavelet-domain FSA has verified a signal candidate it extracts a vector of features from analysis of the shoulder regions. The feature vector extracted from the (generative) wavelet FSA is simply the frequencies on wavelet sum and difference shoulder states for the first (main) shoulder. (Although multi-shoulder recognition and characterization is implemented, only analysis on the first shoulder is needed for the signals herein) In essence, two probability vectors on signal decomposition are being passed to the SVM, one in terms of signal averages and one in terms of signal wavelets (differences). An interpretation of the feature vector as two probability vectors will motivate choices of Kernel function that are based on information theory metrics, such as relative entropy, among others.

The actual operation of the feature extraction phase is accomplished via a single-pass wavelet FSA evaluation that begins in the baseline region prior to the start of the candidate signal indicated by the time-domain FSA (1000 sample point prior to start if possible). By characterizing the baseline prior to the signal, better tracking on the (normalized) value I/Io in the signal shoulder is possible. The preceding baseline analysis also permits characterization of the difference wavelet strength in the baseline, which is used to re-scale the difference wavelet strength in the signal regions prior to quantization. Thus, local normalization is referenced to both baseline current and baseline noise for every signal acquired.

Signal Discrimination

The "feature vectors" deriving from the signals acquired and processed by the FSA stages can be directly cast into an Euclidean space for comparison, i.e., the components of the feature vectors are simply interpreted as Euclidean coordinates. The metric for similarity is simply that induced by the Euclidean space. The aim of such a representation is that points in the Euclidean space from different signal classes should tend to "cluster" into separate groups. Since the relative strength (scaling) of components in the feature vectors can be weighted in any manner deemed appropriate, there is a great deal of freedom in such a representation. In the analysis here a unique scaling is indicated by normalization over the disjoint sub-signal states such that state frequencies are obtained (with a corresponding probability interpretation).

Signal Discrimination via Support Vector Machines (SVMs) is based on the geometric heuristic of hyperplane separability between the signal "clusters", and entails a preliminary "training" phase where the separating hyperplane is obtained. The restriction to absolute separability between signal classes can be relaxed by introduction of a penalty term, and that is what is done in what follows. In its simplest, two-class, implementation the separating hyperplane separates data in one class from data in the other. If there are more than two classes (the usual case) then the SVM is re-trained for each class such that signals from a "query" class (the signal "positives") are on one side of the separating hyperplane, and all other classes are on the other side of the hyperplane. A labeling of "+1" is used on signals from the query, or "positive," class, and the labeling on non-query class signals, or "negatives," is "−1" (recall that for training data such labelings would be known). In training for discrimination between four hairpin molecules that differ in their 5' overhangs there would then be four choices of query class, each with it's own SVM implementation.

If the feature vector for the $i^{th}$ signal is represented as $x_i \in R^m$ (i.e., with "m" components in feature vector), and with labeling $y_i \in \{\pm 1\}$, then a training set of N signals is given by $\{(x_1, y_1), \ldots, (x_N, y_N)\}$. For hyperplane separability, elements of the training set must satisfy the following conditions:

$$\omega \cdot x_i - b \geq +1 \text{ for } y_i = +1,$$

$$\omega \cdot x_i - b \leq -1 \text{ for } y_i = -1,$$

for some values of the coefficients ω and b. This can be written more concisely as:

$$y_i(\omega \cdot x_i - b) - 1 \geq 0,$$

where the data points that satisfy the equality in the above are known as "support vectors" (or "active constraints"). Once training is complete, discrimination is based solely on position relative to the discriminating hyperplane $\omega \cdot x_i - b = 0$, which is defined solely in terms of the support vectors. Since the discrimination done after training only refers to the "support vector" data points, and not all the training data, discrimination is comparatively quick and efficient.

The boundary hyperplanes on the two classes of data are separated by a distance $2/\|\omega\|$, known as the "margin." By increasing the margin between the separated data as much as possible the optimal separating hyperplane is obtained. In the usual SVM formulation, the goal to maximize $\|\omega\|^{-1}$ is restated as the goal to minimize $\|\omega\|^2$. Minimization on $\|\omega\|^2$, taken together with the need to satisfy the inequality constraints above, can be expressed in terms of a Lagrangian variational formulation with optimization defined at a saddle point:

$$L(\omega, b; \alpha) = \|\omega\|^2/2 - \Sigma_i \alpha_i [y_i(\omega \cdot x_i - b) - 1], \alpha_i \geq 0 \forall i,$$

where a minimum is sought on $\{\omega, b\}$ variations and a maximum is sought on $\alpha_i$ variations [ref Luenberger]. If $[y_i(\omega \cdot x_i - b) - 1] > 0$, then maximization on $\alpha_i$ is achieved for $\alpha_i = 0$. If $[y_i((\omega \cdot x_i - b) - 1] = 0$, then there is no constraint on $\alpha_i$. If $[y_i(\omega \cdot x_i - b) - 1] < 0$, there is a constraint violation, and $\alpha_i \to \infty$. If absolute separability is possible the last case will eventually be eliminated for all $\alpha_i$, otherwise its natural to limit the size of $\alpha_i$ by some constant upper bound, i.e., $\max(\alpha_i) = C$. This is equivalent to another set of inequality constraints with $\alpha_i \leq C$. Introducing a new set of Lagrange multipliers, "$\xi_i$", to achieve this the Lagrangian becomes:

$$L(\omega, b; \alpha) = \|\omega\|^2/2 - \Sigma_i \alpha_i [y_i(\omega \cdot x_i - b) - 1] + \Sigma_i \xi_i (C - \alpha_i), \alpha_i \geq 0 \text{ and } \xi_i \geq 0 \forall i.$$

If rewritten as:

$$L(\omega, b; \alpha) = \|\omega\|^2/2 - \Sigma_i \alpha_i [y_i(\omega \cdot x_i - b) - 1 + \xi_i] + \Sigma_i \xi_i C, \alpha_i \geq 0 \text{ and } \xi_i \geq 0 \forall i.$$

then the interpretation of $\xi_i$ as a "slack" variable is clearer, with "penalty" governed by the size of the cutoff constant "C."

At the variational minimum on the {ω,b} variables the Lagrangian simplifies to:

$$L(\alpha) = \Sigma_i \alpha_i - \frac{1}{2}\Sigma_{i,j}\alpha_i\alpha_j y_i y_j x_i \cdot x_j, \ 0 \leq \alpha_i \leq C \forall i, \ \Sigma_i \alpha_i y_i = 0,$$

where only the variations that maximize in terms of the $\alpha_i$ remain (this is known as the Wolfe Transformation). In this form the computational task is greatly simplified. By introducing an expression for the discriminating hyperplane:

$$f(x_i) = \omega \cdot x_i - b = \Sigma_j \alpha_j y_j x_j \cdot x_i - b,$$

the variational solution for $L(\alpha)$ reduces to the following set of relations (known as the Karush-Kuhn-Tucker, or KKT, relations):

$$\text{if } \alpha_i = 0 \Leftrightarrow y_i f(x_i) \geq 1,$$

$$\text{if } 0 < \alpha_j < C \Leftrightarrow y_i f(x_i) = 1,$$

$$\alpha_i = C \Leftrightarrow y_i f(x_i) \leq 1.$$

When the KKT relations are satisfied for all of the $\alpha_i$ (with $\Sigma_i \alpha_i y_i = 0$ maintained) the solution is achieved. (The constraint $\Sigma_i \alpha_i y_i = 0$ is satisfied for the initial choice of multipliers by setting the α's associated with the positives to $1/N^{(+)}$ and the α's associated with the negatives to $1/N^{(-)}$, where $N^{(+)}$ is the number of positives and $N^{(-)}$ is the number of negatives.)

Once the Wolfe transformation is performed it becomes apparent that the training data (support vectors in particular) enter into the Lagrangian solely via the term "$x_i \cdot x_j$". Likewise, the discriminator $f(x_i)$, and KKT relations, are also dependent on the data solely via the "$x_i \cdot x_j$" term. Simple geometric interpretations for the "$x_i \cdot x_j$" term are possible in a variety of instances. One such instance is for data vectors normalized such that $\Sigma_k (x_i^k)^2 = 1$, where "$x_i^k$" is the $k^{th}$ component of the $i^{th}$ feature vector. In such a case the data can be represented as points on a N–1 dimensional unit hypersphere (N the dimension of the data vectors). For the normalized feature vectors obtained here, the components satisfy the relation $\Sigma_k (x_i^k) = 1$, but the features could simply be redefined as the square-root of the $x_i^k$'s, in which case the constraint on the new $x_i$ components would transform to the $\Sigma_j (x_i^k)^2 = 1$ form. For data points residing on a unit hypersphere, $x_i \cdot x_j$ is simply the cosine of the angle between the points. Algebraically there is the simple relation:

$$x_i \cdot x_j = (x_i \cdot x_i + x_j \cdot x_j - (x_i - x_j)^2)/2 = 1 - (x_i - x_j)^2/2.$$

The intuitive notion that $x_i \cdot x_j$ should describe some metric for comparison between $x_i$ and $x_j$ is apparent in the above form, where we have the distance term $(x_i - x_j)^2$.

A generalization of the SVM formalism is possible at this juncture by arguing that there is freedom to "re-map" the data analogous to the square-root redefinition employed above. In which case the critical "$x_i \cdot x_j$" term is replaced by a re-mapping to "$g(x_i) \cdot g(x_j)$", where "g" is any monotonically increasing function. The generalization can go even further by arguing that the Euclidean geometric basis was merely a heuristic, in which case generalization by mappings into higher dimensional spaces can be considered. The variety of generalizations achievable from the above can be encapsulated in terms of generalization of $x_i \cdot x_j$ to the family of symmetric positive definite functions (reproducing kernels) satisfying Mercer's conditions. The generalization to reproducing kernels still derives from a heuristic based on a geometric (manifold) construction, however, and in what follows generalizations for "$x_i \cdot x_j$" are considered that stem from information-theoretic as well as geometric heuristics.

The benefit of the various kernel generalizations is the prospect for better separation on the data clusters for the different classes.

The unit hyper-sphere data described above satisfies the exact relation $x_i \cdot x_j = 1 - (x_i - x_j)^2/2$, which suggests a kernel generalization via interpretation of "$1 - (x_i - x_j)^2/2$" as the first two terms in the expansion of an exponential:

$$x_i \cdot x_j \rightarrow \exp(-(x_i - x_j)^2/2\sigma^2),$$

where an additional tuning parameter, "$\sigma^2$" is also introduced. If the restriction to unit hyper-spherical data is now lifted, the result is the familiar Gaussian kernel, with basis function width given by σ. For discrimination on the data considered in this paper the Gaussian Kernel is one of the better performers, placing third best when σ is tuned appropriately. Direct use of the original $x_i \cdot x_j$ form, on the other hand, is one of the worst performers, even for data re-mapped by the square-root function as described above (and allowing for tuning freedom via generalization to "$x_i \cdot x_j / \sigma^2$").

If the "distance" term in the Gaussian is denoted $d_G = |x_i - x_j| = \sqrt{(\Sigma_k (x_j^k - x_i^k)^2)}$, the Gaussian Kernel can be written as $K_G(x_i, x_j) = \exp(-(d_G)^2/2\sigma^2)$. In general, exponential "regularization" of a metric on the feature vectors, as in the Gaussian, will provide a Kernel satisfying Mercer's conditions [ref]. Since the "kernels" considered in what follows are an extension from those justified by the geometric heuristic to those justified by an information-theoretic heuristic (the final arbiter of performance being empirical results), the key property from the above, in obtaining alternate kernels, will be the exponential "regularization." A number of different kernel families are explored, and they generally fall into two groups: exponential regularization on a distance function or exponential regularization on a (information) divergence.

It is found that a simple stability property ties together the best performing kernels from the various cases. For the Gaussian kernel the stability property is exhibited when the log Kernel variation on feature vector components is calculated:

$$\partial \ln(K_G(x_i, x_j))/\partial x_i^k = (x_j^k - x_i^k)/\sigma^2,$$

where "$x_i^k$" is the $k^{th}$ component of the $i^{th}$ feature vector and "stability" is indicated by the sign of the difference term $(x_j^k - x_i^k)$. An alternate kernel uses just the sign of the difference as an "indicator" function:

$$\partial \ln(K_I(x_i, x_j))/\partial x_i^k \propto \text{sign}(x_j^k - x_i^k)/\sigma^2,$$

where the choice of the integrating factor $\sqrt{(\Sigma_k |x_j^k - x_i^k|)}^{-1}$ leads to the class of kernels:

$$K_I(x_i, x_j) = \exp(-\sqrt{(\Sigma_k |x_j^k - x_i^k|)}/2\sigma^2).$$

The subscript "I" in "$K_I$" is meant to denote "indicator" kernel. For suitable choice of tuning parameter σ, the indicator kernel offers the best performance on the data sets considered.

Rather than use a "stability" indicator based on the difference "$(x_j^k - x_i^k)$", another class of kernels is obtained by use of the ratio "$(x_j^k / x_i^k)$". (In order to avoid singular terms the feature vectors are restricted to have nonzero components.) In order to maintain the "stability" properties of "$(x_j^k - x_i^k)$": $x_j^k > x_i^k \rightarrow$ positive value, $x_j^k = x_i^k \rightarrow$ zero value, and $x_j^k < x_i^k \rightarrow$ negative value, the ratio expression actually needed is "$(x_j^k / x_i^k) - 1$". Interestingly, the ratio expression $\ln(x_j^k / x_i^k)$ also suffices in this regard, and this offers a helpful piece of information since the "stability" indicator based on the combination "$x_j^k/x_i^k)-1+\ln(x_j^k/x_i^k)$" is directly integrable:

$$\partial \ln(K_{SE}(x_i, x_j))/\partial x_i^k = ((x_j^k/x_i^k)-1+\ln(x_j^k/x_i^k))/2\sigma^2,$$

$$K_{SE}(x_i, x_j) = \exp(-[D(x_i\|x_j)+D(x_j\|x_i)]/2\sigma^2),$$

where "SE" in "$K_{SE}$" is meant to denote "symmetric entropic" kernel, and the expression $D(x_i\|x_j)$ is the familiar relative entropy (or "information divergence") between "probability vectors" $x_i$ and $x_j$. The symmetric-entropic kernel provides the second best discrimination performance on the data sets considered. Since the feature vectors can be interpreted as probabilities, and satisfy the probability relation $\Sigma_k(x_i^k)=1$, it is, perhaps, not surprising that the symmetric-entropic kernel should be a good performer.

The other kernel families considered stem from explorations along the lines presented above. Since the relative entropy function, $D(x_i\|x_j)$, is positive definite on "probabilistic" data (satisfying $\Sigma_k(x_i^k)=1$), asymmetric positive definite functions are also considered in the kernels explored. Performance for the two asymmetric choices of entropic kernel, however, (where one or the other of the relative entropies in the symmetric-entropic kernel is dropped) is generally very poor.

The SVM implementation used in this analysis solves the KKT relations via a variant of a procedure known as Sequential Minimal Optimization (SMO). The SMO method of solution is more efficient than most other methods and is greatly simplified in its implementation since much of the computation is circumvented by existence of analytical reductions. The method begins by selecting a pair of Lagrange multipliers, $\{\alpha_1,\alpha_2\}$, where at least one of the multipliers has a violation of its associated KKT relations (for simplicity it is assumed in what follows that the multipliers selected are those associated with the first and second feature vectors: $\{x_1, x_2\}$). The selection process on Lagrange multipliers in the implementation here uses a variation of the SMO heuristic that focuses on KKT violators, and this is one of the means by which the method is able to efficiently go about obtaining a solution to the maximization problem on $L(\alpha)$. Once the multipliers are selected, a maximization on $L(\alpha)$ is sought with only those multipliers allowed to vary ($\alpha_1$ and $\alpha_2$ in what follows):

$$L((\alpha_1,\alpha_2;\alpha_{i\geq 3})=\alpha_1+\alpha_2-(\alpha_1^2$$

$$K_{11}+\alpha_2^2 K_{22}+2\alpha_1\alpha_2 y_1 y_2 K_{12})/2-\alpha_1 y_1 v_1$$

$$-\alpha_2 y_2 v_2+$$

$$\Sigma_i \alpha_i - \tfrac{1}{2}\Sigma_{i,j} \alpha_i \alpha_j y_i y_j K_{ij}, \text{ with } i,j\geq 3,$$

where $K_{ij}\equiv K(x_i, x_j)$, and $v_i\equiv \Sigma_j \alpha_j y_j K_{ij}$ with $j\geq 3$. Due to the constraint $\Sigma_i \alpha_i y_i=0$, we have the relation:

$$\alpha_1+s\alpha_2=-\gamma,$$

where $\gamma\equiv y_1\Sigma_i \alpha_i y_i$ with $i\geq 3$ and $s\equiv y_1 y_2$. Substituting the constraint to eliminate references to $\alpha_1$, and performing the variation on $\alpha_2$:

$$\partial L(\alpha_2;\alpha_{i\geq 3})/\partial \alpha_2=(1-s)+\eta\alpha_2+s\gamma(K_{11}-K_{22})+sy_1 v_1-y_2 v_2,$$

where $\eta\equiv(2K_{12}-K_{11}+K_{22})$. Since $v_i$ can be rewritten as $v_i=\omega\cdot x_i-\alpha_1 y_1 K_{i1}-\alpha_2 y_2 K_{i2}$, the variational maximum $\partial L(\alpha_2;\alpha_{i\geq 3})/\partial \alpha_2=0$ leads to the following update rule:

$$\alpha_2^{new}=\alpha_2^{old}-y_2((\omega\cdot x_1-y_1)-(\omega\cdot x_2-y_2))/\eta.$$

Once $\alpha_2^{new}$ is obtained, the constraint $\alpha_i\leq C$ must be re-verified in conjunction with the $\Sigma_i \alpha_i y_i=0$ constraint. If the $L(\alpha_2;\alpha_{i\geq 3})$ maximization leads to a $\alpha_2^{new}$ that grows too large, the new $\alpha_2$ must be "clipped" to the maximum value satisfying the constraints. For example, if $y_1\neq y_2$, then increases in $\alpha_2$ are matched by increases in $\alpha_1$. So, depending on whether $\alpha_2$ or $\alpha_1$ is nearer its maximum of C, we have $\max(\alpha_2)=\text{argmin}\{\alpha_2+(C-\alpha_2); \alpha_2+(C-\alpha_1)\}$. Similar arguments provide the following boundary conditions:

Case 1, s=−1

$$\max(\alpha_2)=\text{argmin}\{\alpha_2; C+\alpha_2-\alpha_1\},$$

$$\min(\alpha_2)=\text{argmax}\{0; \alpha_2-\alpha_1\},$$

Case 2, s=+1

$$\max(\alpha_2)=\text{argmin}\{C; \alpha_2+\alpha_1\},$$

$$\min(\alpha_2)=\text{argmax}\{0; \alpha_2+\alpha_1-C\},$$

In terms of the new $\alpha_2^{new, \, clipped}$, clipped as indicated above if necessary, the new $\alpha_1$ becomes:

$$\alpha_1^{new}=\alpha_1^{old}+s(\alpha_2^{old}-\alpha_2^{new, \, clipped}),$$

and $s\equiv y_1 y_2$ as before.

After the new $\alpha_1$ and $\alpha_2$ values are obtained there still remains the task of obtaining the new "b" value. If the new $\alpha_1$ is not "clipped" then the update must satisfy the non-boundary KKT relation: $y_1 f(x_1)=1$, i.e., $f^{new}(x_1)-y_1=0$. By relating $f^{new}$ to $f^{old}$ the following update on b is obtained:

$$b^{new1}=b-(f^{new}(x_1)-y_1)-y_1(\alpha_1^{new}-\alpha_1^{old})K_{11}-y_2(\alpha_2^{new, \, clipped}-\alpha_2^{old})K_{12}.$$

If $\alpha_1$ is clipped but $\alpha_2$ is not, the above argument holds for the $\alpha_2$ multiplier and the new b is:

$$b^{new2}=b-(f^{new}(x_2)-y_2)-y_2(\alpha_2^{new}-\alpha_2^{old})K_{22}-y_1(\alpha_1^{new, \, clipped}-\alpha_1^{old})K_{12}.$$

If both $\alpha_1$ and $\alpha_2$ values are clipped then any of the b values between $b^{new1}$ and $b^{new2}$ is acceptable, and following the SMO convention, the new b is chosen to be: $b^{new}=(b^{new1}+b^{new2})/2$. (If the feature vectors satisfy the hyper-sphere constraint described earlier the algorithm can be sped up by simply fixing b, the hyper-plane shift value, to be zero, thereby avoiding the computational expense of the above b update.)

In the SMO algorithm caching is performed on the updated $f(x_i)$ values so that the $\alpha$ updates can be performed without redundant computations. Although it introduces a memory constraint, similar caching is done in this study on the kernel evaluations and a noticeable speed-up is obtained.

Devices

The devices employed in the subject methods are nanopore devices, as described more fully above. Preferably the subject devices further include an algorithm, as described above. As indicated above, the algorithm may be part embedded in the hardware processing component of the device, or present on software that may or may not be removable from the device.

Kits

Also provide are kits for use in practicing the subject methods. The kits at least include a computer readable storage medium on which is recorded an algorithm, as described above. The computer readable storage medium may be any convenient medium, including CD, DAT, floppy disk, etc. Alternatively, a website or other remote access means may be present in the kit which enables one to obtain the algorithm. Where desired, the kit may further include additional reagents for performing a particular application. For example, kits specifically directed to sequencing nucleic acids through the subject methods may be included, where the kits may further include enzymatic activities necessary for producing the overhangs and blunt ends which are required for practicing the subject methods, as described above. Furthermore, the kits will generally include instructional material for carrying out the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way of illustration and not by way of limitation.

Experimental

I. Rapid Discrimination Among Individual DNA Molecules at Single Nucleotide Resolution Using a Nanopore Instrument

A. Experimental Protocol

1. DNA hairpin design, synthesis, and purification. DNA oligonucleotides as reported in Table 1 below were synthesized using an ABI 392 Synthesizer, purified by PAGE, and stored at −70° C. in TE buffer. The length of the DNA hairpin stems was varied by adding or removing base pairs from a well-characterized six base pair hairpin as reported in Senior, et al., *Proc Natl Acad Sci USA* 85, 6242–6246 (1988). Unless otherwise noted, the hairpin loops were composed of four deoxythymidine nucleotides, and both ends of the hairpin stems were closed with G:C or C:G base pairs. The prediction that each hairpin would adopt one base-paired structure was tested and confirmed using the DNA mfold server found at the website (http://mfold.wustl.edu/~folder/dna/form1.cgi). Control linear DNA strands had the same base compositions as the hairpins, but the primary sequences were scrambled so that stable duplex stem regions could not form.

TABLE 1

| SEQ ID NO: | 1 | 2 | 3 | 4 | 5 | 6 | 7 | 8 | 9 | 10 | 11 |
|---|---|---|---|---|---|---|---|---|---|---|---|
| Predicted Hairpin Secondary Structure | TT<br>T T<br>G:C<br>C:G<br>C:G<br>5'  3' | TT<br>T T<br>G:C<br>C:G<br>A:T<br>C:G<br>5'  3' | TT<br>T T<br>G:C<br>C:G<br>A:T<br>A:T<br>G:C<br>5'  3' | TT<br>T T<br>G:C<br>C:G<br>A:T<br>A:T<br>G:C<br>C:G<br>5'  3' | TT<br>T T<br>G:C<br>C:G<br>A:T<br>A:T<br>G:C<br>T:A<br>C:G<br>5'  3' | TT<br>T T<br>G:C<br>C:G<br>A:T<br>A:T<br>G:C<br>T:A<br>T:A<br>C:G<br>5'  3' | TT<br>T T<br>G:C<br>C:G<br>A:T<br>A:T<br>G:C<br>C:G<br>T:A<br>T:A<br>C:G<br>5'  3' | T<br>T T<br>G:C<br>C:G<br>A:T<br>A:T<br>C:G<br>5'  3' | TT<br>T T<br>G:C<br>C:G<br>A:T<br>A A<br>G:C<br>C:G<br>5'  3' | TT<br>T T<br>G:C<br>C:G<br>A:T<br>A:T<br>G:C<br>T:A<br>C:G<br>T 3'<br>5' | TT<br>T T<br>G:C<br>C:G<br>A:T<br>A:T<br>G:C  3'<br>C:G  5'<br>T:A<br>T:A<br>G:C<br>C:G<br>T  T<br>T  T |
| Identity | 3 bp | 4 bp | 5 bp | 6 bp | 7 bp | 8 bp | 9 bp | 5 bp<br>3 dT | 6 bp A$_{14}$ | 7 bp<br>5' dT | Dumbbell |
| ΔG$^b$ (Kcal/mol) | −3.0 | −4.5 | −5.6 | −8.2 | −9.0 | −11.4 | −12.8 | −4.2 | −4.3 | −9.8 | −11.3 |
| I/Io$^c$ (%) | 68 | 64 | 60 | 52 | 47 | 35 | 32 | 62 | 53 | 45 | NA |
| Blockade Duration (median in ms) | 0.8 | 5 | 68 | 760 | 3200 | NA | NA | 21 | 5 | 3700 | NA |

$^a$DNA oligonucleotides were synthesized using an ABI 392 Synthesizer, purified by PAGE, and stored at −70° C. in TE buffer.
$^b$ΔG values for hairpin formation were calculated using the DNA mfold server (http://mfold.wustl.edu/~folder/dna/form1.cgi) based on data from SantaLucia (1998) (14). Assume 22° C. and 1 M KCl.
$^c$I is the current average for an event shoulder (in pA). I$_0$ is the current average for the open channel (in pA).

2. Formation of α-hemolysin pores in horizontal bilayers. Each experiment was conducted using one α-hemolysin channel inserted into a diphytanoyl-phosphatidylcholine/hexadecane bilayer across a 20 micron diameter horizontal Teflon aperture, as described previously (Akeson et al., *Biophys J* 77, 3227–3233 (1999) and Kasianowicz et al., *Proc Natl Acad Sci USA* 93, 13770–13773 (1996)). See also WO 00/28312; the disclosure of which is herein incorporated by reference. Seventy microliter chambers on either side of the bilayer contained 1.0M KCl buffered at pH 8.0 (10 mM HEPES/KOH). Voltage was applied across the bilayer between Ag—AgCl electrodes that were re-plated each day. DNA was added to the cis chamber giving a 10 μM final concentration unless otherwise noted. All experiments were conducted at room temperature (22±1° C.).

The above described nanopore device was formed by an α-hemolysin channel inserted in a lipid bilayer. X-ray diffraction analysis of the assembled protein reveals a heptamer with a 2.6 nm aperture leading into a slightly wider vestibule that abruptly narrows to a transmembrane domain with a 1.5 nm constriction. In 1.0 M KCl (pH 8.0), a 120 mV applied potential produces a steady open channel current ($I_o$) of 120±5 pA (FIG. 1, a). Translocation of single-stranded linear DNA reduces this current to I≅14 pA ($I/I_o$=12%). Each monomer within the single stranded DNA traverses the length of the 10-nm pore in 1 to 3 µs.

3. Data acquisition and analysis. Ionic current was filtered at 100 kHz bandwidth using a low pass Bessel filter and recorded at 5 µs intervals (200 kHz) using an Axopatch 200B amplifier (Axon Instruments, Foster City, Calif.) coupled to an Axon Digidata 1320A digitizer. Applied potential was 120 mV (trans side positive) unless otherwise noted. Manual analysis of shoulder blockade current and duration was performed using Fetchan 6.0.6.01 on data filtered at 10 kHz using a digital low pass Gaussian filter (Axon Instruments, Foster City, Calif.).

4. Support Vector Machine learning. Blockade events from each data file were recognized and cut out using a customized Finite State Automaton (FSA), and then passed to the SVM. SVM classification requires a training phase and a test phase. In its training phase, an SVM learns to distinguish one class of blockade events (the query class) from all other blockade events using separate data files. SVM scores cover a range (from +3 to −3 in our experiments) with positive scores given to events that fit the query class criteria and negative scores given to events that do not fit the query class criteria. Scores near zero are ambiguous. After training, the SVM is tested on independent mixed data. In the analysis of the DNA molecule signals, the vectors fed to the SVM were based on: i) blockade shoulder duration, average, minimum, maximum, and standard deviation of I/Io for the entire blockade shoulder; ii) minimum, maximum, and standard deviation of I/Io over each of ten time-domain bins; iii) and a wavelet profile based on averaging the fifth-order wavelet coefficients derived from the signal for the whole event. The statistical measures for SVM are sensitivity and specificity. Sensitivity is defined as true positives/(true positives+false negatives)) and specificity is defined as true positives/(true positives+false positives). A true positive is an event in the test data that comes from the positive class and is assigned a positive value; a false positive occurs when the SVM assigns a positive score to an event in the test data when that event actually comes from the negative class. A false negative is an event that is assigned a negative value, but actually comes from the positive class. These values provide a measure of how well the SVM was able to discriminate among classes of data.

B. Results and Discussion

1. Use of DNA Hairpins to Model Duplex DNA Interaction with the Nanopore.

We chose DNA hairpins as model duplexes because they can be formed from short, highly pure oligonucleotides that can be designed to adopt one base-paired structure in 1.0 M salt at room temperature. The initial experiments involved a well-characterized DNA hairpin with a six-base-pair stem and a four-deoxythymidine loop. When captured within an α-hemolysin nanopore, this molecule caused a partial current blockade (or 'shoulder') lasting hundreds of milliseconds (FIG. 1, b) followed by a rapid downward spike (FIG. 1, c). This "shoulder-spike" signature is consistent with two sequential steps: i) capture of a hairpin stem in the vestibule, where the molecule rattles in place because the duplex stem cannot fit through the 1.5-nm diameter-limiting aperture of the pore; and ii) simultaneous dissociation of the six base pairs in the hairpin stem, thus allowing the extended single-strand to traverse the channel. This type of signature describes approximately 60% of blockade events caused by the 6 base pair hairpin. The remaining events varied in amplitude and were less than one millisecond in duration. These fast events are explained by interactions of the hairpin loop with the mouth of the pore without entry into the vestibule.

We tested our explanation of the shoulder-spike signature using a series of blunt-ended DNA hairpins with stems that ranged in length from 3 to 9 base-pairs, corresponding to SEQ ID NOS:1–11 (Table 1). If the model described above is accurate, we would expect a substantial increase in blockade shoulder lifetime for each additional base pair and a modest linear increase in the lifetime of the downward spike at the end of the event. We would also expect the shoulder amplitude to decrease as the stem length increased. These predictions proved to be correct. Each base pair addition resulted in a measurable increase in median blockade shoulder lifetime that correlated with the calculated $\Delta G°$ of hairpin formation (FIG. 2). Increasing stem length resulted in a 10 µs increase in median duration of the terminal spike. A downward trend in shoulder current amplitude was also observed from $I/I_o$) equal to 68% for a 3 bp stem to $I/I_o$) equal to 32% for a 9 bp stem (Table 1). Our results are consistent with greater obstruction of ionic current as the hairpin stem extends further into the vestibule with each additional base pair.

The model described above also assumes that the hairpin loop is unable to enter the vestibule. Using a molecular dynamics simulation (AMBER field)(Michael, D., Edn. 3.01 (Pyramid Learning LLC, Hudson, Ohio; 1999)) we found that the four-deoxythymidine loop of these hairpin molecules adopted conformations that would prevent ready entry into the pore vestibule. We tested this using a DNA 'dumbbell' with 4dT loops at either end (Table 1). If the loop cannot enter the vestibule, interaction of dumbbell hairpins with the pore would not result in the shoulder-spike signature. When we examined the dumbbell hairpins experimentally, fast blockades (less than 1 ms) were observed, but shoulder-spike blockades were not.

2. Identification of Individual DNA Molecules at Single Base Pair Resolution.

Figure 3A:
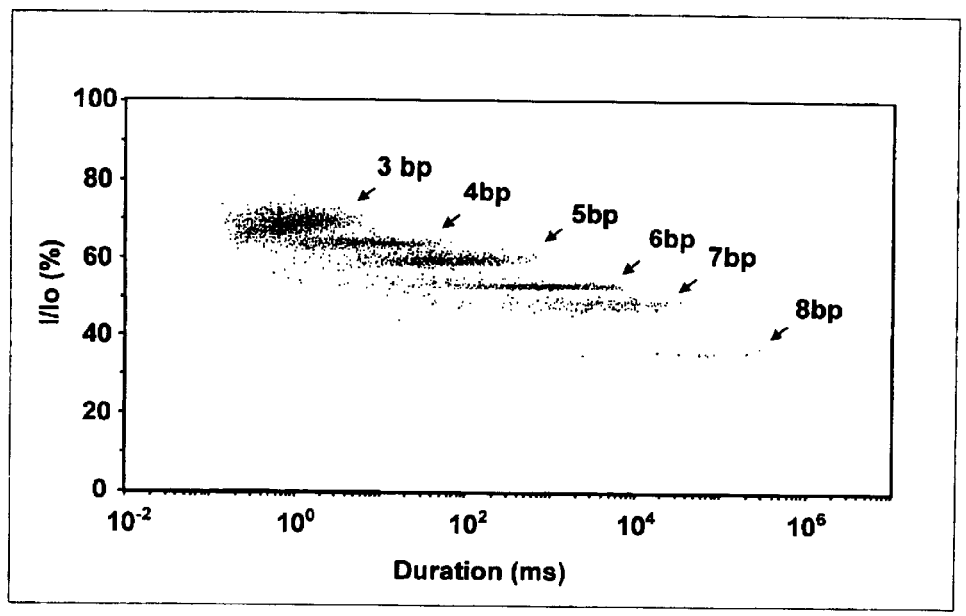
FIG. 3. Discrimination between DNA hairpins at single base-pair resolution. a, Event diagram for DNA hairpins with 3 to 8 base-pair stems. Events were selected for adherence to the shoulder-spike signature. Each point represents the duration and amplitude of a shoulder blockade caused by one DNA hairpin captured in the pore vestibule. The data for each hairpin are from at least two different experiments run on different days. Median $I/I_o$ values for each type of hairpin varied by at most 2%. The duration of the 9 bp hairpin blockade shoulders were too long for us to record a statistically significant number of events. Control oligonucleotides with the same base compositions as the DNA hairpins, but scrambled, caused blockade events that were on average much shorter than the hairpin events and that did not conform to the shoulder-spike pattern. b, Classification of the 6bp hairpin (solid bars) versus all other hairpins (open bars) by SVM. Note the log scale on the Y axis. The dashed lines mark the limits of the rejection region. The boundaries of the rejection region were determined by independent data, not post hoc, on the data shown. The events that were rejected were primarily fast blockades similar to those caused by loops on the dumbbell hairpin (Table 1) or acquisition errors caused by the low selectivity threshold of the FSA.
FIG. 3c provides the structures of differing hairpin molecules and their respective current blockade profiles.

The strength of the nanopore instrument is discrimination among individual DNA molecules at high speed and high resolution. This is illustrated by an $I/I_o$ vs duration plot of 3 to 8 bp hairpin blockade events that were screened manually for adherence to the shoulder-spike signature (FIG. 3a). The identity of a large majority of DNA hairpin molecules could be visually discerned and the single base-pair difference between individual molecules was easily resolved. The high level of discrimination visible in FIG. 3a was confirmed using an automated procedure for recognition of signal regions followed by signal classification using a Support Vector Machine (SVM)(Vapnik, V. The Nature of Statistical Learning Theory, Edn. 2nd. (Springer, 1999); Burges, C. J. C. A tutorial on Support Vector Machines for pattern recognition. *Data Mining and Knowledge Discovery* 2, 121–167 (1998)). SVMs provide a scalable means to represent data in a higher dimensional space where discrimination can be achieved by a hyper-plane dividing that space. This provides a uniform method to classify individual blockade signatures acquired by the nanopore instrument. In brief, blockade events from each data file were recognized and cut out using a customized Finite State Automaton (FSA) (Cormen, T. H., Leiserson, C. E. & Rivest, R. L. Introduction to Algorithms. (McGraw-Hill, 1989)). The FSA was less stringent than the shoulder-spike criterion used in FIG. 3a, and included any event that exceeded 200 µs in duration and $I/I_o$ less than 85%. Approximately twice as many signals were passed by the FSA as met the shoulder-spike diagnostic evaluated manually (FIG. 3a), while less than 0.1% of the shoulder-spike signals were rejected. Signal features (see Methods) were extracted and grouped as a 'feature vector' for each event. The feature vectors were used by the SVM to classify each event.

Figure 3B:
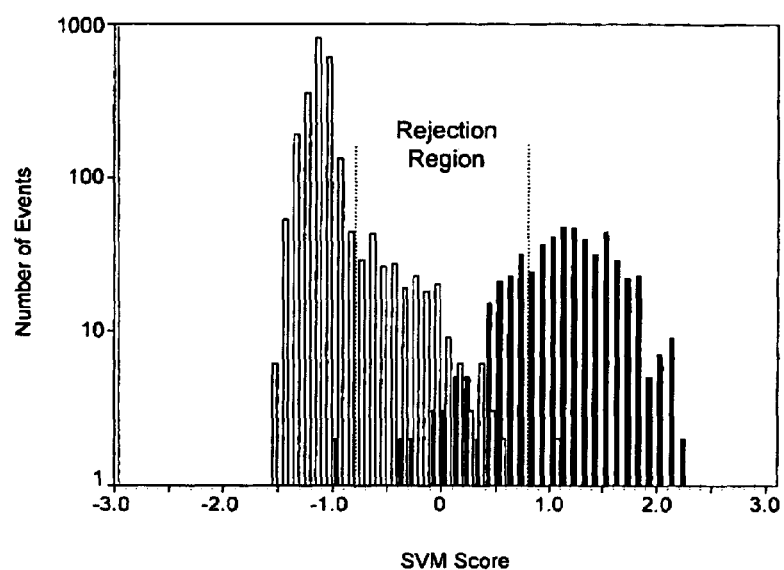

FIG. 3b shows an example where blockade events caused by 6 bp hairpins were classified against blockades caused by 3, 4, 5, 7 and 8 bp hairpins. The FSA passed 529 of the 6bp hairpin events to the SVM and 3185 of all other events. Because selectivity was relaxed at the FSA, there were many ambiguous signals with scores near zero. Using an additional set of independent data, the SVM can be trained to exclude these by introducing a rejection region for the scoring (the region between dashed lines in FIG. 3b). The events that were rejected were primarily fast blockades similar to those caused by loops on the dumbbell hairpin (Table 1) or acquisition errors caused by the low selectivity threshold of the FSA. When 20% of the events were rejected in this manner, the SVM scores for the 6 bp hairpin discrimination achieved a sensitivity of 98.8% and a specificity of 98.8% (see Methods). Similar results were obtained for each class of hairpins depicted in FIG. 3a. Overall the SVM achieved an average sensitivity of 98% and average specificity of 99%. Thus, the stem length of an individual DNA hairpin can be determined at single base-pair resolution using a machine learning algorithm.

Figure 3C:
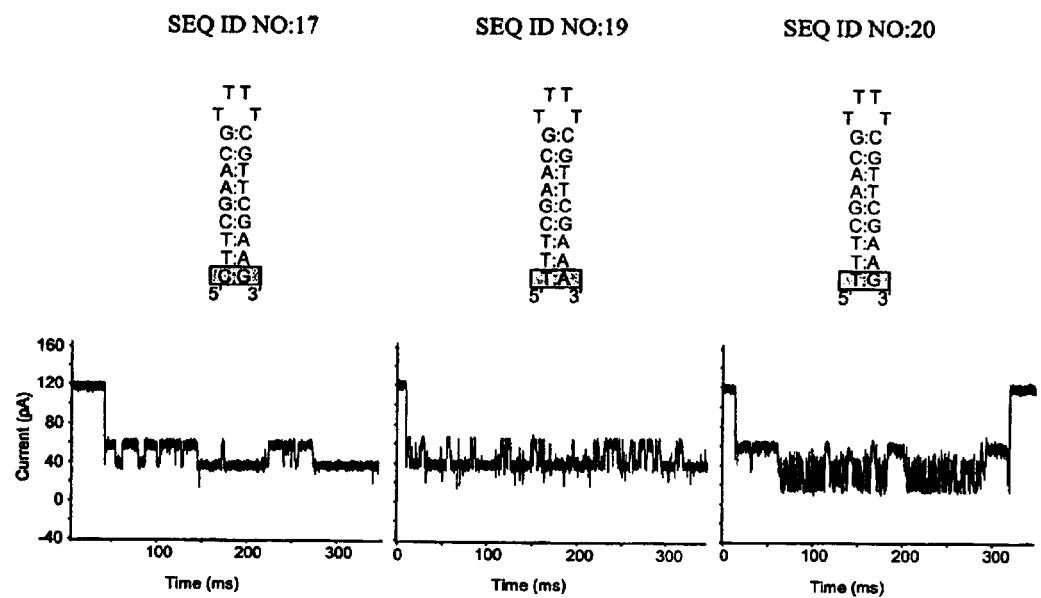

FIG. 3c shows blockade patterns where only the terminal base pair differed between molecules. Thus, individual DNA molecules with terminal G-C (SEQ ID NO:17), A-T (SEQ ID NO:19), and G-T (SEQ ID NO:20) base pairs could be distinguished from one-another.

3. Detection of Single Nucleotide Differences Between Two Otherwise Identical DNA Molecules.

Figure 4:
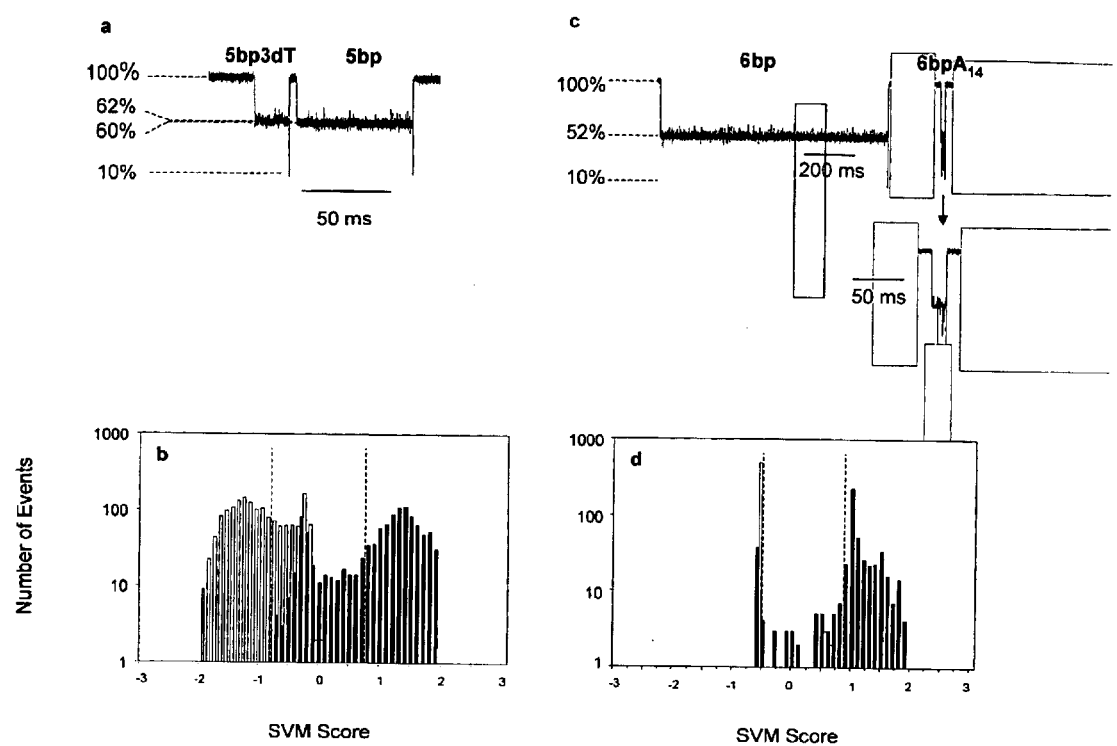
FIG. 4. Detection of single nucleotide differences between DNA hairpins. a, Comparison of typical current blockade signatures for a 5bp hairpin and a 5bp hairpin with a three-dT loop. The standard 5bp hairpin event has a two percent deeper blockade than the 5bp3dT hairpin. b, Histogram of SVM scores for 5bp hairpins (filled bars) versus 5bp hairpins with three-dT loops (clear bars). c, Comparison of typical current blockade signatures for a standard 6bp hairpin and a 6bp hairpin with a single $dA_3$-$dA_{14}$ mismatch in the stem. The 6bp$A_{14}$ event is expanded to show the fast downward spikes. These rapid, near-full blockades and the much shorter shoulder durations are the main characteristics identified and used by SVM to distinguish 6bp$A_{14}$ hairpin events from 6bp hairpin events. d, Histogram of SVM scores for 6bp hairpins (filled bars) versus 6bp$A_{14}$ hairpins (clear bars).

We found that single nucleotide alterations in DNA could be detected using the nanopore instrument Here we present two examples. The first example involved the hairpin loop. A 5bp hairpin with a 3-deoxythymidine loop (5bp3dT in Table 1; SEQ ID NO:8) caused pore blockades in which the shoulder amplitude was increased ≅2 pA and the median shoulder duration (21 ms) was reduced 3-fold relative to the same hairpin stem with a 4-deoxythymidine loop (5 bp in Table 1; SEQ ID NO:3). Typical events are illustrated in FIG. 4a. The FSA acquired 3500 possible 5 bp hairpin signals from ten minutes of recorded data. The SVM classification for this data set (FIG. 4b) gave sensitivity and specificity values of 99.9% when 788 events were rejected as the unknown class. The second example involved the hairpin stem. Introduction of a single base-pair mismatch into the stem of a 6-bp hairpin ($T_{14} \rightarrow A_{14}$, 6 bp$A_{14}$ in Table 1; SEQ ID NQ:9) caused approximately a 100-fold decrease in the median blockade shoulder duration relative to a hairpin with a perfectly matched stem (6 bp in Table 1; SEQ ID NO:4). Typical events are shown in FIG. 4c. This difference in duration is consistent with the effect of a mismatch on $\Delta G°$ of hairpin formation (FIG. 2), and it permitted a 90% separation of the two populations using the manually applied shoulder-spike diagnostic. When analysis was automated, the FSA acquired 1031 possible events from ten minutes of recorded data (FIG. 4d). With the aid of wavelet features (Nievergelt, Y. Wavelets Made Easy. (Birkhauser, Boston; 1999)) that characterize the low frequency noise within the shoulder current, the SVM was able to discriminate the standard 6 bp hairpin (SEQ ID NO:4) from the mismatched 6 bp$A_{14}$ hairpin (SEQ ID NO:9) with sensitivity 97.6% and specificity 99.9% while rejecting only 42 events.

4. A Voltage-Pulse Routine Permits DNA Duplex Analysis Over Short, Defined Time Intervals.

Figure 5:
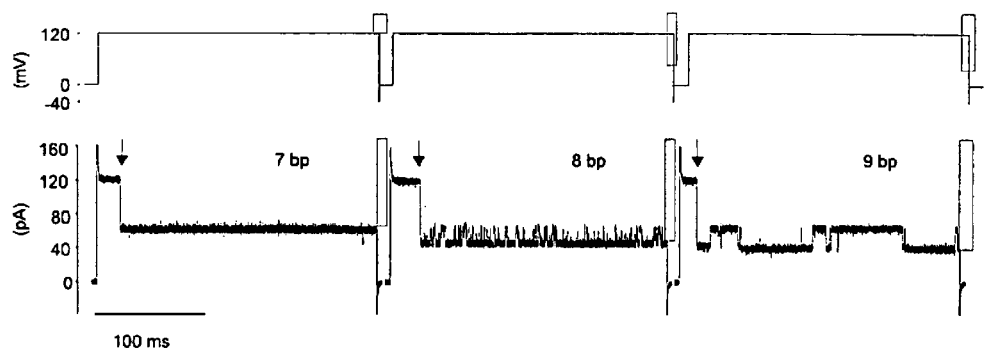
FIG. 5. Typical current blockade signatures caused by 7, 8, and 9 base-pair hairpins obtained using a voltage pulse routine. The top trace represents the voltage waveform applied across a single α-hemolysin channel. The bottom trace represents ionic current through the channel in response to this voltage during a single experiment sampling a mixture of 7, 8, and 9 base-pair hairpins. Each current sweep begins with a capacitance transient followed by a steady current of 122 pA through the open channel. Capture of a hairpin in the pore vestibule (arrows) results in a partial blockade. This ends when the voltage briefly reverses to −40 mV, releasing the hairpin. The blockade events shown for each hairpin length are representative of thousands of events acquired using a single α-hemolysin pore prepared separately on at least three occasions. All experiments were conducted in 1.0 M KCl at 22±1° C. with a 120 mV applied potential. The traces shown were acquired at 100 kHz bandwidth then filtered at 10 kHz with a digital Gaussian filter.

For longer hairpin stems (or for native duplex DNA), very long shoulder blockades preclude rapid identification of each captured molecule. For example, the shoulder duration for a hairpin with as few as 8 base pairs ranged up to 300 seconds resulting in a very small number of measurable events in a 30-minute experiment (FIG. 3a). To overcome this limitation, we modified the acquisition protocol from a fixed +120 mV potential to a voltage pulse routine that toggled between +120 mV for 249.5 ms and −40 mV for 0.1 ms. In essence, the routine was designed to capture and examine each hairpin stem for a finite amount of time under standard conditions then eject the hairpin rather than pulling it through the pore. Representative blockades for 7 bp (SEQ ID NO:5), 8 bp (SEQ ID NO:6), and 9 bp (SEQ ID NO:7) stems using this acquisition protocol are shown in FIG. 5. Shoulder blockades caused by the 8bp and 9bp hairpins toggled between two conductance states. The greater of these states corresponded to the average conductance for the 7bp hairpin. The lesser conductance states for the 8bp and 9bp hairpins were nearly equal with one another, however transitions between the two states were significantly more frequent for the 8bp hairpin than for the 9bp hairpin. We postulate that these two conductance states represent transient interaction of the terminal base pair of the 8 bp and 9 bp hairpins with amino residues in the vestibule wall near the limiting aperture. This explanation predicts that single nucleotide or single base pair modifications at the end of the 8 and 9bp hairpin stems would alter the rate of transition between conductance states.

When analysis of this data set was automated, signals for individual 7, 8, and 9 base pair hairpin molecules were distinguishable from one another in a three-way mixture with average sensitivity 99% and average specificity 96%.

Figure 9:
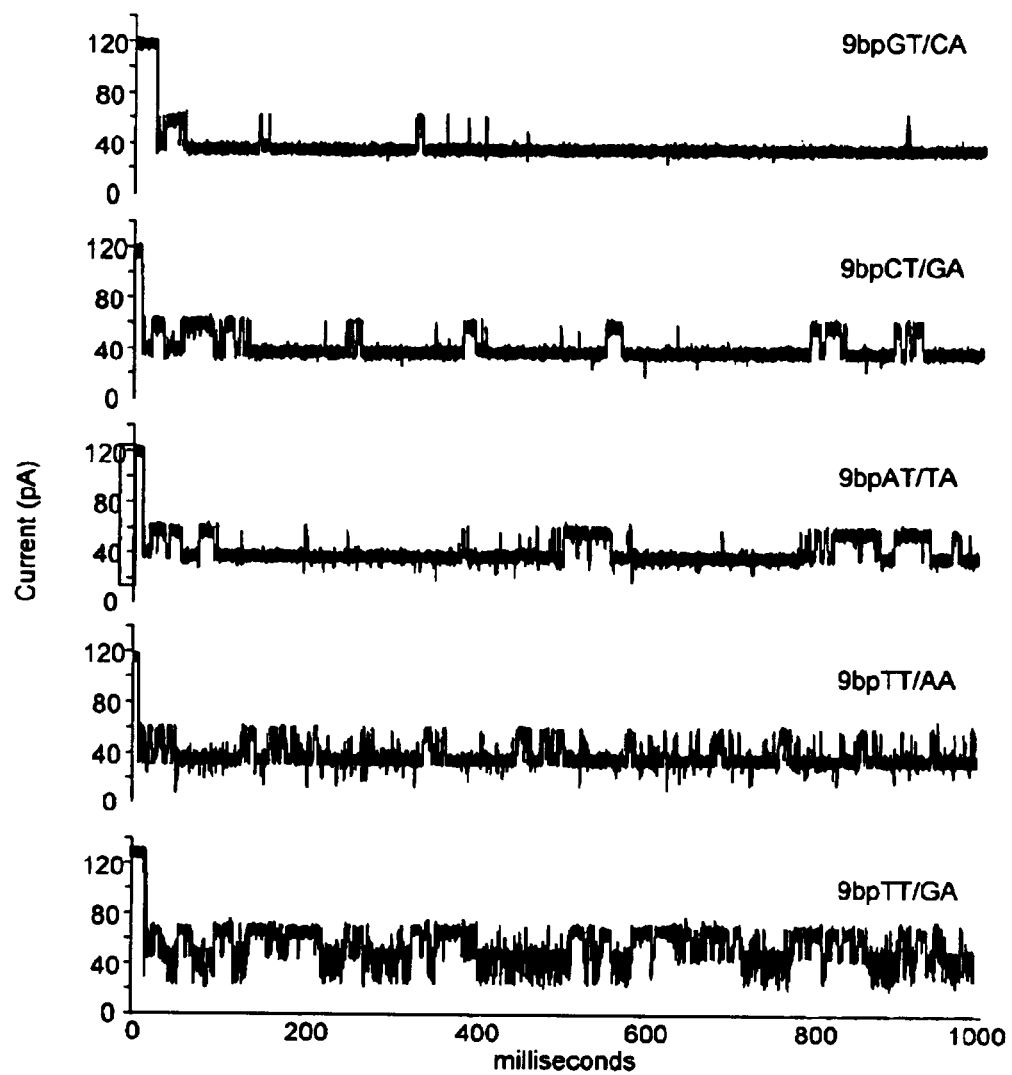
FIG. 9. Blockade of the α-hemolysin pore by 9bp DNA hairpins in which the terminal base pair is varied. Blockade events were acquired at 120 mV applied potential and 23.0° C. (see Methods). Each signature shown is caused by a single hairpin molecule captured in the pore vestibule, and is representative of several thousand single molecule events.
Figure 10:
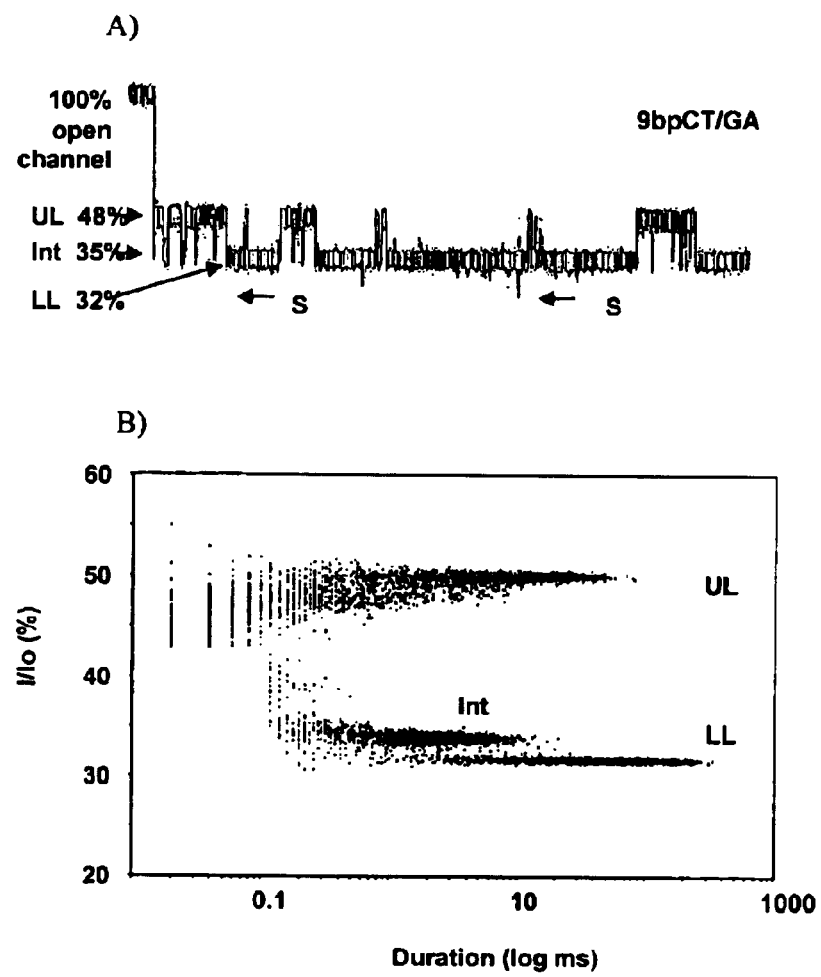
FIG. 10. Representative blockade of ionic current caused by a 9bp DNA hairpin (9bp(GT/CA). Open channel current ($I_o$) is typically 120 pA at 120 mV and 23.0° C. Here it is expressed as 100% current. Capture of a DNA hairpin causes a rapid decrease to a residual current I, expressed as a percent of the open channel current. Typically, 9bp hairpins cause the residual current to transition between four states: an upper conductance level (UL), an intermediate level (IL), a lower level (LL), and a transient downward spike (S). b) A two dimensional plot of log duration vs. amplitude for UL, IL, and LL conductance states.
Figure 11:
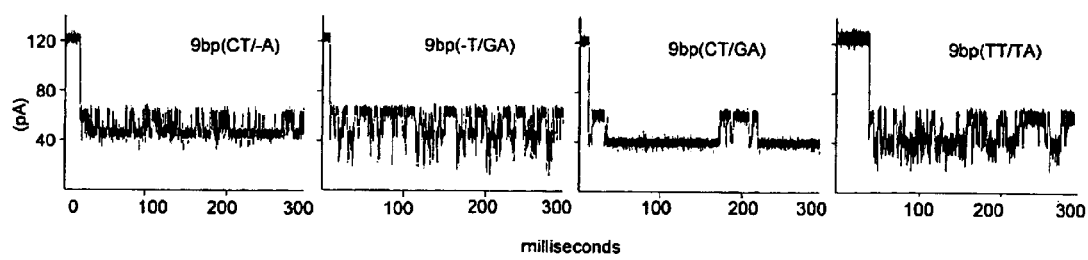
FIG. 11. Comparison of blockade signatures caused by DNA hairpins with dangling and blunt ends. All hairpins were built onto a core 8bp DNA hairpin with the primary sequence 5'-TTCGAACGTTTTCGTTCGAA-3'. 9bp(CT/-A) shows a blockade signature caused by a hairpin with a dangling 5'-C nucleotide. 9bp(-T/GA) shows a blockade signature caused by a dangling 3'-G nucleotide. 9bp(CT/GA) shows a blockade signature for a hairpin in which both terminal nucleotides are present forming a 5'-C•G-3' terminal Watson-Crick base-pair. 9bp(TT/TA) shows a typical blockade signature for a blunt-ended 9bp hairpin in which the terminal 5'-T•T-3' pair is weakly associated. Experimental conditions are described under Methods.

5. Discrimination Among Individual Watson-Crick Base-Pairs at the Termini of Single DNA Hairpin Molecules The nanopore device can also be used to discriminate among the four permutations of Watson-Crick base pairs at 9bp DNA hairpin termini. The DNA hairpins we used are shown in Table 2 and are abbreviated as 9bp(CT/GA; SEQ ID NO:13), 9bp(GT/CA; SEQ ID NO:12), 9bp(TT/AA; SEQ ID NO:15), and 9bp(AT/TA; SEQ ID NQ:14) where the two letters before the slash are the first two bases in the hairpin sequence reading from 5'-to-3', and the two letters after the slash are the last two bases in the hairpin sequence reading from 3'-to-5'. Table 2 appears in FIG. 8: Examples of thousands of pore blockades for each of these hairpins are shown in FIG. 9. Terminal base-pair identity can be determined by kinetic analysis of the nanopore data. In particular, average dwell time in the lower conductance level (LL in FIG. 10) and the frequency of downward current spikes (S in FIG. 10) are highly dependent upon the presence of a base pair in the ninth position. This is illustrated in FIG. 11 where neither a 5' dC dangling nucleotide nor a 3' dC dangling nucleotide alone stabilized ionic current in the lower level (I/Io 32%), whereas both nucleotides together (the CG pair) did so. It was conceivable that the presence of two nucleotides alone at the terminus of the hairpin stem could account for this current stabilization. However, two weakly paired thymine bases at the blunt end terminus of a 9bp hairpin stem resulted in an unstable blockade signature (FIG. 11). In practice, the lower conductance level has the added advantage that transitions to UL are stochastic, and that one first order exponential can be fit to the dwell time distribution giving a time constant ($\tau_{LL}$) in the millisecond range.

Figure 12:
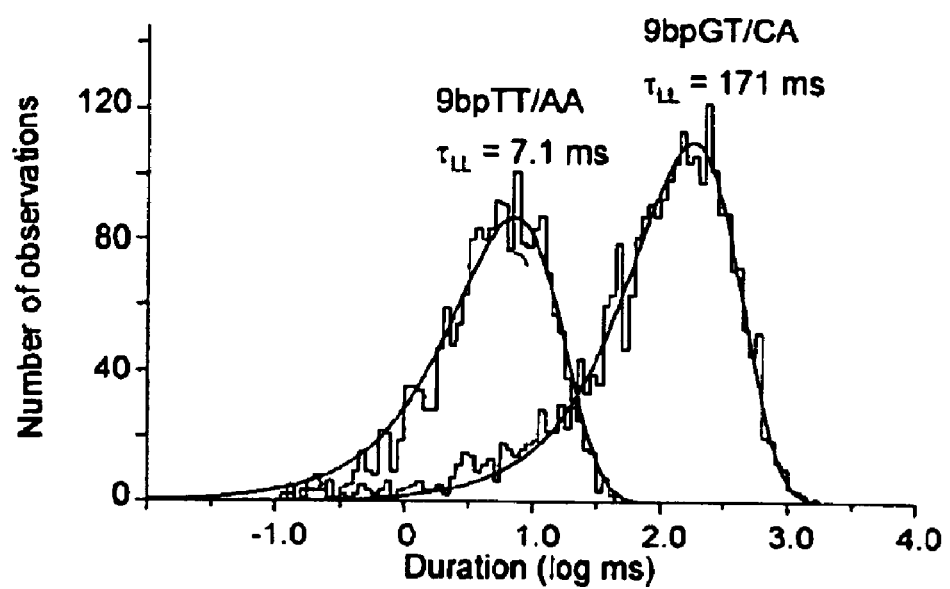
FIG. 12. Dwell time histograms for lower level (LL) blockade events. Duration measurements were plotted in semi-log frequency histograms with 20 bins per decade. At least 1000 measurements of duration were used for each plot. To determine the probability density function and the average event lifetime, $\tau_{LL}$, curves were fit to each histogram using the Levenberg-Marquardt method. 9bp(TT/AA) is the standard 9bp hairpin with a 5'-T•A-3' terminus, and 9bp(GT/CA) is a 9bp hairpin with a 5'-G•C-3' terminus.

To test the sensitivity of the lower level conductance state to Watson-Crick base-pair identity, we measured $\tau_{LL}$ and spike frequency for the four 9bp hairpins whose blockade signatures are illustrated in FIG. 9. Dwell time histograms for the lower conductance state caused by 9bp(GT/CA; SEQ ID NO:12) and by 9bp(TT/AA; SEQ ID NO:15) are shown in FIG. 12. First-order exponentials fit to similar histograms for all four permutations of Watson-Crick base-pairs reveal $\tau_{LL}$ values ranging from 160 ms to 7 ms in the order 9bp(GT/CA; SEQ ID NO:12)>9bp(CT/GA; SEQ ID NQ:13) >9bp(AT/TA; SEQ ID NO:14)>9bp(TT/AA; SEQ ID NO:15) (Table 3).

TABLE 3

Comparison between single DNA hairpin kinetic parameters and $\Delta\Delta G°$ for terminal base-pairs. $\Delta\Delta G°_{term}$ values are the difference between calculated $\Delta G°$ of duplex formation for 9bp DNA hairpins and calculated $\Delta G°$ of duplex formation for core 8bp hairpins that lack the terminal base-pair. Calculations assumed 23.0 C. and 1 M KCl. They were performed using Mfold (http://bioinfo.math.rpi.edu/~mfold/dna/form1.cgi) which is based on data from SantaLucia (SantaLucia, J., Jr. A unified view of polymer, dumbbell, and oligonucleotide DNA nearest-neighbor thermodynamics. Proc Natl Acad Sci USA 95, 1460–5 (1998).). Spike frequency and $\tau_{LL}$ values are means ± standard errors for at least three experiments using different individual channels.

| Identity | $\tau_{LL}$ ms | Spike frequency $s^{-1}$ | $\Delta\Delta G°$ term kcal/mol |
|---|---|---|---|
| 9bpGT/CA (SEQ ID NO:12) | 160 ± 23 | 4 ± 1 | −1.9 |
| 9bpCT/GA (SEQ ID NO:13) | 50 ± 4 | 12 ± 4 | −1.8 |
| 9bpAT/TA (SEQ ID NO:14) | 43 ± 5 | 34 ± 10 | −1.2 |
| 9bpTT/AA (SEQ ID NO:15) | 7 ± 1 | 91 ± 47 | −1.3 |
| 9bpTT/GA (SEQ ID NO:16) | 6 ± 2 | 1300 ± 400 | −0.3 |

The reverse order is observed for the spike frequency ranging from 4 spikes $s_{-1}$ (9bp(GT/CA; SEQ ID NO.12)) to 82 spikes $s^{-1}$ (9bp(TT/AA; SEQ ID NO.15)). Thus, two easily measured kinetic parameters can be used to discriminate among Watson-Crick base pairs on single DNA molecules.

One of the more difficult base-pairs to recognize using conventional hybridization arrays is a terminal mismatch, in particular a TG wobble pair. To test the sensitivity of the nanopore to this mismatch, we compared blockade signatures caused by a hairpin composed of the sequence 9bp (TT/GA; SEQ ID NO.16) with blockade signatures caused by the wild-type sequences 9bp(CT/GA; SEQ ID NO.13) and 9bp(TT/AA; SEQ ID NO.15) (FIG. 9). All individual blockades that exhibited the characteristic four current level signature could be identified as one of these molecules. Quantitative examination of the data revealed that spike frequency was the key diagnostic parameter. That is, there was a statistically significant difference between spike frequencies caused by each of the three termini, i.e. 12 spikes $s^{-1}$ (9bp(CT/GA; SEQ ID NO.13)), 82 spikes $s^{-1}$ (9bp(TT/AA; SEQ ID NO.15)), and 1400 spikes $s^{-1}$ (9bp(TT/GA; SEQ ID NO.16)) (Table 2). In contrast, $\tau_{LL}$ values were statistically different between 9bp(TT/GA; SEQ ID NO.16) and 9bp(CT/GA; SEQ ID NO.13) termini, but not between 9bp(TT/G6; SEQ ID NO.15) and (9bp(TT/AA; SEQ ID NO.15) termini (Table 3). It appears that $\tau_{LL}$ values plateau in the low millisecond time-range for any blunt-ended DNA terminus regardless of base-pair stability.

The rankings of spike frequency and $\tau_{LL}$ correlate with conventional estimates of terminal base-pair stability. Table 3 lists free energy values for terminal base pairs ($\Delta\Delta G°_{Term}$) calculated using the online computational tool 'Mfold' (http://bioinfo.math.rpi.edul/~mfold/dna/form1.cgi) which is based on a nearest neighbor model of duplex stability. In Table 3, the $\Delta\Delta G°_{Term}$ values are the difference between the free energy of duplex formation for a given 9bp hairpin and the free energy of duplex formation of a common 8bp core hairpin sequence. Among Watson-Crick base pairs, $\Delta\Delta°_{Term}$ values ranged from −1.9 kcal/mol for 9bp(GT/CA; SEQ ID NO:12) to −1.2 kcal/mol for 9bp(AT/TA; SEQ ID NO:14). $\Delta\Delta G°_{Term}$ for the TG wobble pair was calculated to be −0.3 kcal/mol. In general, the rank of spike frequency and $\tau_{LL}$ correlated with $\Delta\Delta G°_{Term}$, however the correlation is imperfect in that the expected order of 9bp(TT/AA; SEQ ID NO:15) and 9bp(AT/TA; SEQ ID NO:14) was reversed. There are several possible explanations for this discrepancy including uncertainty surrounding the predicted stability of terminal 5'-A•T-3' and 5'-T•A-3' pairs[2,7], and limits on the precision of optical melting curves that underlie the free energy calculations. We note that the calculated $\Delta\Delta G°_{Term}$ values for the 9bp(AT/TA; SEQ ID NO:14) and 9bp(TT/AA; SEQ ID NO:15) termini differed by only 0.1 kcal/mol (Table 3) which is smaller than the 5% precision given for Mfold. It is also important to note that base-pair stability is influenced by the electric field (data not shown) and possibly by amino acids in the vestibule wall. The magnitude of these effects could be sequence dependent, thus altering the stability ranking in the nanopore assay relative to a bulk solution assay.

Non-Covalent Forces that Influence $\tau_{LL}$ and Spike Frequency

Having established a general correlation between the nanopore data and classical measures of base-pair stability, we determined if non-covalent forces that contribute to DNA duplex stability could be detected by the nanopore. Forces that stabilize DNA duplexes include hydrogen bonding between bases, and base stacking. Forces that destabilize DNA duplexes include hydrogen bonding between water molecules and nucleotide bases, and electrostatic repulsion between phosphodiester anions in the DNA backbone. Steric effects may stabilize or destabilize the duplex depending upon sequence context.

Initial inspection of the data in Table 3 suggests that hydrogen bonding plays a significant role in spike frequency and $\tau_{LL}$. That is, terminal base pairs that are known to form three hydrogen bonds when paired (GC and CG) are more stable than base-pairs that are known to form two hydrogen bonds when paired (AT, TA, and TG). However, in practice it is difficult to assign a stability change to hydrogen bonding alone. This is illustrated by comparing the TG wobble pair and the CG Watson-Crick base-pair. In substituting a 5' thymidine for a 5' cytosine at the 9bp hairpin terminus, hydrogen bond number is reduced from three to two, but stacking energy is stabilized by −0.1 kcal/mol as shown by melting curves for DNA duplexes with dangling ends. Although small, this change in stacking energy is comparable to calculated differences in $\Delta\Delta G°_{Term}$ between some of the terminal base-pairs in Table 3. Thus, the change in blockade signature associated with the CG→TG terminal substitution is due to the combined effect of added stacking stabilization by thymine and destabilization by loss of hydrogen bonds. Competing effects are also likely when the thymine in the terminal TA base-pair is replaced by difluorotoluene (9bpTT/AA→9bpFT/AA; SEQ ID NO:18). Difluorotoluene is a near perfect structural mimic of thymine that is recognized nearly as well by DNA polymerases despite the absence of hydrogen bonding to paired adenines.

Figure 13:
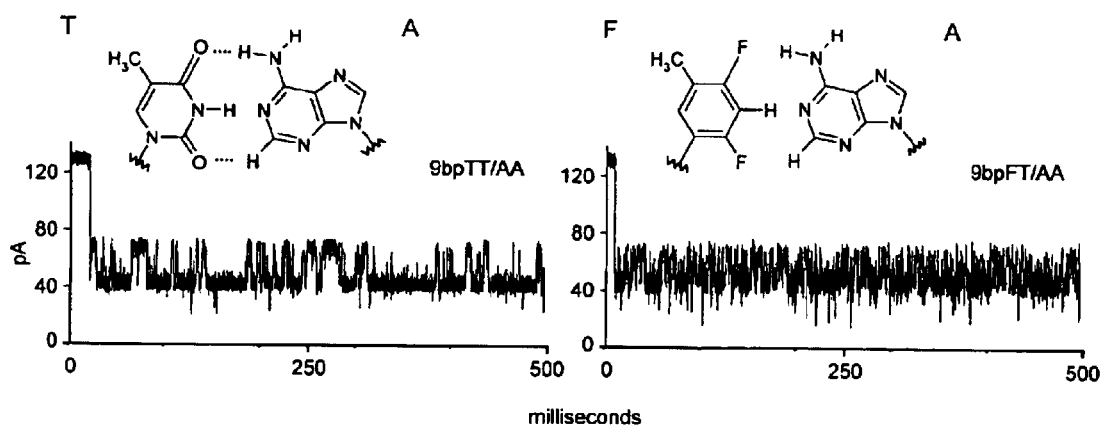
FIG. 13. Effect of difluorotoluene (F) substitution for thymine (T) on blockades caused by 9bp hairpins. The blockade signature at left is caused by a 9bp hairpin with a 5'-T•A-3' terminus (9bp(TT/AA) in Table 1). The blockade signature at right is caused by a nearly identical 9bp hairpin in which the 5' thymine is replaced by difluorotoluene (9bp(FT/AA) in Table 1) giving a 5'-F•A-3' terminus which lacks hydrogen bonds. The blockade signatures shown are representative of thousands of single molecule events acquired under standard conditions (see Methods).

This isostere would be an ideal tool to assess the influence of hydrogen bonding on $\tau_{LL}$ and spike frequency, however, difluorotoluene is nonpolar and its stacking interaction with neighboring bases stabilizes the duplex by −1.5 kcal/mol relative to thymine. Thus, the blockade signature due to 9bpTT/AA→9bpFT/AA (SEQ ID NO:18) (FIG. 13) is a conservative measure of destabilization due to loss of hydrogen bonding because it is partially offset by added stacking stability.

The data in Table 3 also indicate that orientation of the bases in the terminal pair influences spike frequency and $\tau_{LL}$. That is, flipping the terminal base-pair so that a purine is on the 5′ side and a pyrimidine is on the 3′ side (9bp(CT/GA SEQ ID NO:13)→9bp(GT/CA; SEQ ID NO:12) and 9bp(TT/AA; SEQ ID NO:1 5)→9bp(AT/TA; SEQ ID NO:14)) consistently increased $\tau_{LL}$ and decreased spike frequency. Among Watson-Crick base-pairs, the size of this effect equals or exceeds the effect of increasing hydrogen bond number (Table 3). Classical thermodynamic studies suggest two possible explanations: i) stacking forces with the neighboring base-pair are altered when the terminal base-pair is flipped; and ii) stacking of bases at the 5′ position of a duplex can be different from those at the 3′ position independent of the neighboring base-pair. To test the first explanation, we compared $\tau_{LL}$ for the standard 9bp hairpins containing the four possible Watson-Crick termini (Table 2 at left) with their counterparts in which the penultimate TA base-pair was flipped, i.e. hairpins 9bp(TA/AT; SEQ ID NO:22), 9bp(AA/TT; SEQ ID NO:21), 9bp(CA/GT; SEQ ID) NO:20) and 9bp(GA/CT; SEQ ID NO:19) at right in Table 2. 9bp(TT/AA; SEQ ID NO:15) was the least stable of the original sequences with $\tau_{LL}$ equal to 7 ms. By making the substitution 9 bp(TT/AA; SEQ ID NO:15)→9 bp(TA/AT; SEQ ID NO:22), $\tau_{LL}$ was increased about three-fold to 20 ms (Table 4).

TABLE 4

Effect of penultimate base-pair orientation on $\tau_{LL}$ for 9bp hairpins with different Watson-Crick base-pair termini. Values shown represent means ± standard errors for at least three different individual channels. Experimental conditions are described under Methods.

| Terminal Base-Pair | Penultimate Base-Pair | |
|---|---|---|
| | 5′-T•A-3′ | 5′-A•T-3′ |
| | $\tau_{LL}$ in milliseconds ± S.E. | |
| 5′-T•A-3′ | 7 ± 1 | 20 ± 4 |
| 5′-A•T-3′ | 43 ± 5 | 30 ± 6 |
| 5′-G•C-3′ | 160 ± 23 | 210 ± 90 |
| 5′-C•G-3′ | 50 ± 4 | 66 ± 20 |

Conversely, 9 bp(AT/TA; SEQ ID NO:14) was the most stable of the thymidine/adenine termini with $\tau_{LL}$ equal to 43 ms. By making the same alteration of the neighboring base-pair as in the previous experiment, 9 bp(AT/TA; SEQ ID NO:14)→9 bp(AA/TT; SEQ ID NO:21), $\tau_{LL}$ was decreased to 30 ms. Thus, stacking against the neighboring base-pair did account for much of the stability difference associated with orientation of the thymine/adenine termini. The independent effect of placing adenine at the 5′ position was small. For the guanine/cytosine termini, the outcome was very different (Table 3). In those cases, flipping penultimate base pairs did not significantly effect $\tau_{LL}$. Thus, the three-fold difference in $\tau_{LL}$ for 5′-G•C-3′ versus 5′-C•G-3′ is due to an end-specific effect independent of the neighboring base-pair.

An obvious application of existing nanopore technology is detection of single nucleotide mismatches in duplex DNA (e.g. single nucleotide polymorphisms (SNPs) or point mutations). It has been shown that single mismatches in hairpin stems or in duplexes formed between solution strands and probe strands covalently bound to the α-hemolysin vestibule can be discerned based on dwell time of the duplex in the pore vestibule. Although this single parameter has some utility, it is limited in that the identity and the position of the mismatch cannot be known. It is also likely that such a detection strategy would suffer from false reads as do DNA hybridization arrays (e.g. misreads at duplex termini or at wobble pairs). By comparison, it has been shown in this and a previous study[1] that mismatches can result in distinctive sequence-specific blockade signatures entirely apart from dwell time.

In summary, we have shown that a nanopore device can be used to discriminate among Watson-Crick base pairs at blunt-ended termini of individual DNA hairpin molecules based on two kinetic parameters. Hydrogen bonding, sequence-specific stacking to neighboring base-pairs, and nucleotide orientation at the terminus contribute to the observed differences in blockade signatures.

C. Conclusions

From the above results, we conclude that a prototype nanopore detector coupled with machine learning algorithms can resolve single nucleotide or single base-pair differences between otherwise identical duplex DNA molecules. Unlike other single DNA molecule assays, this nanopore instrument examines DNA molecules in solution without chemical modification, amplification, or adsorption to a solid surface. Thousands of molecules can be examined and classified in minutes.

The above results show that nanopore instruments find utility in assays where single nucleotide resolution is important, and where analysis must be conducted at high speed with a small sample. Applications where such devices therefore find use include in vitro detection of DNA damage (e.g. depurination and thymine dimerization), measurement of duplex stability changes caused by nucleotide modifications, enzyme kinetics, and DNA sequence analysis.

II. DNA Sequencing Strategy Using a Nanopore Detector in Voltage Pulse Mode

The sequencing approach is diagrammed in FIG. 6A to 6G. Duplex DNA with blunt ends is prepared by any of a number of conventional methods. In principle, any length of DNA may be used, including intact chromosomes. This DNA fragment is modified so that one end can be bound to a protecting molecule or surface such that enzymatic digestion from that end cannot occur (FIG. 6a). The protecting molecule or surface can be, but is not limited to, an oligonucleotide that forms a triplex at the protected end, or a synthetic bead to which the protected end is bound. The opposite end of the duplex is unprotected and is thus subject to enzymatic digestion. A population of the cloned DNA molecule, or a single copy of the DNA molecule, is then digested sequentially by a combination of exonucleases. An example using Exonuclease III and Mung Bean nuclease is shown in FIGS. 6b–g. Exonuclease III is a non-processive enzyme that cuts the 3 prime end from duplex DNA leaving 5 prime overhangs. In the example shown, digestion conditions are regulated so that only one nucleotide is cut from the duplex end leaving a one nucleotide overhang on the 5 prime end (FIG. 6b). The identity of the 5 prime nucleotide is read by the nanopore detector while it is captured in the pore vestibule by an applied voltage (FIG. 6c). Once the identity of the end is established the voltage is reversed, releasing the duplex end from the nanopore (FIG. 6d). If necessary, the end of the same molecule or of another molecule may be recaptured and read before the enzymatic digestion proceeds. Once the identity of the overhanging nucleotide is established, the DNA is cut with Mung Bean nuclease leaving a blunt end (FIG. 6e). This end is examined with the nanopore, establishing the identity of the terminal base pair (FIG. 6f). The two step digestion is then repeated numerous times until each nucleotide in the DNA duplex is established (FIG. 6g). By reading both the 5 prime overhang generated by exo III digestion, and the blunt end generated by Mung Bean nuclease digestion in order, the analytical system proof reads the sequence that is generated.

III.

A. Signal Classification Results for 9 bp Hairpins.

Channel current blockades due to nanopore-captured DNA Hairpin molecules differing only in their terminal base pairs are rapidly distinguished using the methods discussed above. The molecules are correctly classified greater than 99.9% of the time when presented as in silico mixtures with equal contributions from the different species. The molecules differentiated share the same 8 base-pair hairpin (8 bphp) base, and are formed into four distinct 9 bphps by the addition of one of the (four) Watson-Crick base-pairs. Together with an 8 bphp control, classification is described between five molecules. The signal processing architecture is designed to be scalable, i.e., to easily extend to discrimination on many more signals than five. If scalability is relaxed, allowing class-specific HMM processing for example, class-specific feature extractions can be used to boost discrimination accuracy further.

Figure 14:
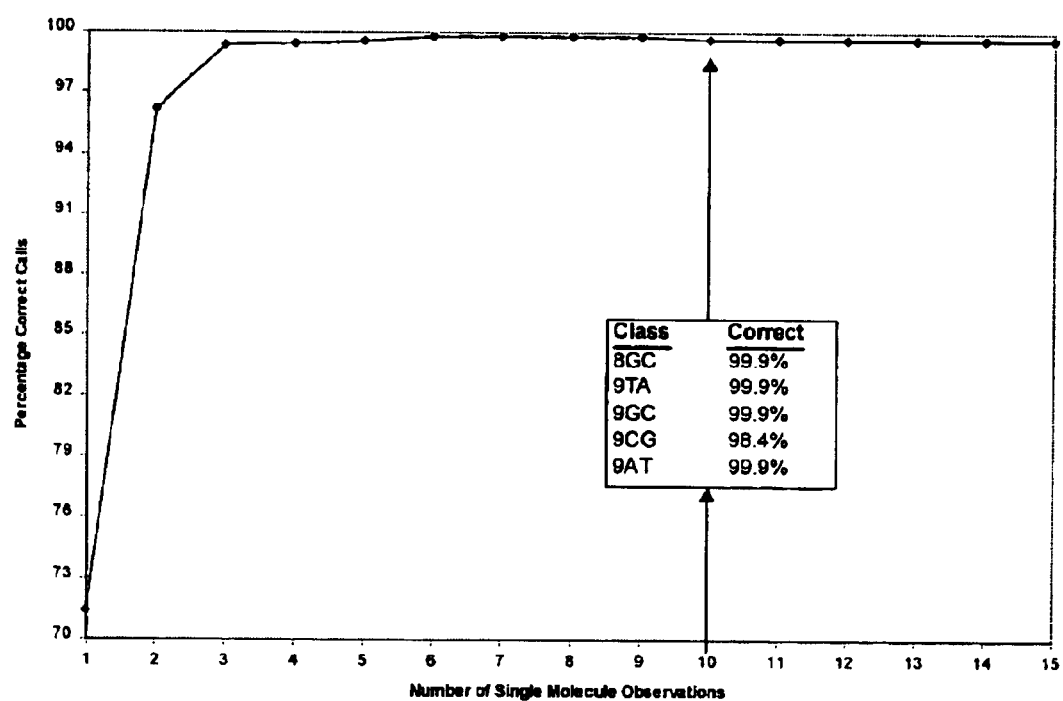
FIG. 14 provides graphical results of experimental data reported in the Experimental Section, below.

The signal acquisition, feature extraction, and discrimination all operate in real-time on 100 msec current blockade measurements. With no-capture cycles factored in, the single DNA molecule capture-measure-eject process has an effective duty cycle of one classification every 0.4 seconds. Most of the signal processing time (on-line) is spent at the HMM/EM feature extraction stage, while the bulk of the discrimination processing is effectively done off-line, during the training of the SVM classifiers. The signal rejections are typically very high, about 85%, to obtain optimal calling conditions. If a ten-fold redundancy in molecule sampling/classifications is used (FIG. 14) 85% rejection can be maintained. Ten molecule samplings lead to DNA terminus classification with better than 99.9% accuracy (see FIG. 14), and has throughput about one call every four seconds with the present nanopore instrument.

B. Mixture Evaluation. The data analysis so far has been based on train files that are approximately pure, and the multi-class discrimination results are for in silico mixtures. The goal is to analyze mixtures in solution, and preliminary results for identifying mixtures of two classes from (9TA, 9GC, 9CG, 9AT) show an accuracy of better than 96% on calling their respective proportions. The added complication with true mixture calling derives from the need to calibrate for the different acceptance rates on molecules by the pore and the different rejection rates of the classifier. It is found for mixtures of two classes that the critical calibration constant linking signal count ratios to molecule concentration ratios varies by less than 4%. In further work with the nanopore detector it may be possible to observe real-time population dynamics in the presence of enzymatic activity using this technology.

It is evident from the above discussion and results that the subject invention provides an important new way to characterize, analyze and distinguish duplex nucleic acid molecules at the single nucleotide or single base pair level. The subject methods and protocols are rapid, occur in solution and may be automated to a significant extent, e.g., with the use of appropriate algorithm driven computing means. In certain protocols, the duplex nucleic acids need not be chemically modified, amplified or bound to a solid support. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of characterizing an unlabeled duplex nucleic acid molecule, said method comprising:
   (a) contacting a conducting fluid medium comprising said unlabeled duplex nucleic acid with a nanopore;
   (b) applying an electric field to said medium and monitoring current changes through said nanopore resulting from said unlabeled duplex nucleic acid to obtain a set of observed data values;
   (c) evaluating said set of observed data values to identify a duplex nucleic acid specific signal; and
   (d) characterizing said unlabeled duplex nucleic acid molecule based on said identified duplex nucleic acid specific signal.

2. The method according to claim 1, wherein said set of observed data values is manipulated in characterizing said duplex nucleic acid.

3. The method according to claim 2, wherein said duplex nucleic acid is characterized in terms of a signature current blockade profile or portion thereof.

4. The method according to claim 1, where said applied electric field is constant.

5. The method according to claim 1, wherein said applied electric field is pulsed.

6. A method of identifying the presence of an unlabeled duplex nucleic acid molecule in a conducting fluid medium, said method comprising:
   (a) contacting said conducting fluid medium with a nanopore;
   (b) applying an electric field to said medium;
   (c) monitoring current changes through said nanopore to obtain a set of observed data values;
   (d) evaluating said set of observed data values to identify a duplex nucleic acid specific signal; and
   (e) determining whether said unlabeled duplex nucleic acid is present in said conducting fluid medium from said a duplex nucleic acid specific signal identified (d).

7. The method according to claim 6, wherein said duplex nucleic acid molecule is a duplex DNA molecule.

8. The method according to claim 6, wherein said applied electric field is constant.

9. The method according to claim 6, wherein said applied electric field is pulsed.

10. The method according to claim 6, wherein said conducting fluid medium includes a plurality of different duplex nucleic acids that differ from each other by sequence.

11. The method according to claim 6, wherein said determining step (d) is performed by an automated means.

12. The method according to claim 6, wherein said determining step (d) is manually performed.

13. A method of determining the sequence of a duplex DNA molecule, said method comprising:
   (a) providing a fluid conducting medium comprising said duplex DNA molecule as a molecule that is protected at one end and blunt-ended at the other end;
   (b) producing a single nucleotide overhang at said blunt end of said duplex DNA molecule;
   (c) contacting said fluid conducting medium with a nanopore;
   (d) applying an alternating electric field to said fluid conducting medium and monitoring current changes through said nanopore resulting from said duplex nucleic acid to obtain a set of observed data values;
   (e) removing said single nucleotide overhang from said duplex DNA molecule;
   (f) repeating steps (b) to (e) to obtain a collection of sets of observed data values for each different duplex nucleic acid produced from said original duplex nucleic acid, and
   (g) determining the sequence of said duplex DNA molecule from said collection of sets of observed data values;
   to sequence said duplex DNA molecule.

14. The method according to claim 13, wherein said determining step (g) is determined by an automated data processing means.

15. A nanopore device for characterizing an unlabeled duplex nucleic acid molecule, said device comprising:
   an algorithm for characterizing an unlabeled duplex nucleic acid molecule based on evaluating observed current modulations through a nanopore to identify a duplex nucleic acid specific signal, wherein said algorithm is present on a computer readable medium.

16. A kit for use in characterizing an unlabeled duplex nucleic acid molecule, said kit comprising:
   an algorithm for characterizing an unlabeled duplex nucleic acid molecule based on evaluating observed current modulations through a nanopore to identify a duplex nucleic acid specific signal, wherein said algorithm is present on a computer readable medium.

17. A kit for use in sequencing a duplex DNA molecule, said kit comprising:
   a first enzyme that produces a single nucleotide overhang comprising duplex DNA molecule from a blunt ended duplex DNA molecule; and
   a second enzyme that produce a blunt-ended duplex DNA molecule from a duplex DNA molecule that comprises a single nucleotide overhang.

18. The kit according to claim 17, wherein said first enzyme is an exonuclease.

19. The kit according to claim 17, wherein said second enzyme is a nuclease.

20. The kit according to claim 17, wherein said kit further comprises an algorithm for characterizing a duplex nucleic acid molecule based on observed current modulations through a nanopore, wherein said algorithm is present on a computer readable medium.

* * * * *